(12) United States Patent
Murakami

(10) Patent No.: US 7,131,983 B2
(45) Date of Patent: Nov. 7, 2006

(54) ULTRASONIC SURGICAL INSTRUMENT

(75) Inventor: Eiji Murakami, Hachioji (JP)

(73) Assignee: Olympus Corporation (JP)

( * ) Notice: Subject to any disclaimer, the term of this patent is extended or adjusted under 35 U.S.C. 154(b) by 602 days.

(21) Appl. No.: 10/336,957

(22) Filed: Jan. 6, 2003

(65) Prior Publication Data
US 2003/0135136 A1     Jul. 17, 2003

(30) Foreign Application Priority Data
Jan. 11, 2002 (JP) ............................. 2002-005103
Dec. 6, 2002 (JP) ............................. 2002-355608

(51) Int. Cl.
*A61B 17/32* (2006.01)
*A61B 17/20* (2006.01)

(52) U.S. Cl. ........................................ 606/169; 604/22
(58) Field of Classification Search ................ 606/169; 604/22
See application file for complete search history.

(56) References Cited

U.S. PATENT DOCUMENTS

| 5,322,055 | A |   | 6/1994  | Davison et al. ................ 601/2 |
| 5,582,588 | A |   | 12/1996 | Sakurai et al. |
| 5,776,155 | A | * | 7/1998  | Beaupre et al. .............. 606/169 |
| 6,099,537 | A | * | 8/2000  | Sugai et al. ................. 606/143 |
| 6,206,844 | B1|   | 3/2001  | Reichel et al. |
| 6,328,703 | B1|   | 12/2001 | Murakami ...................... 601/4 |
| 2002/0107538 | A1 |  | 8/2002 | Shibata et al. |

FOREIGN PATENT DOCUMENTS

WO     WO 99/35982     7/1999

OTHER PUBLICATIONS

Search Report from European Patent Office dated May 6, 2003.

* cited by examiner

*Primary Examiner*—Michael Peffley
*Assistant Examiner*—Alex Toy
(74) *Attorney, Agent, or Firm*—Ostrolenk, Faber, Gerb & Soffen, LLP

(57) ABSTRACT

When a probe unit and a sheath unit are coupled to each other, an engaging portion of the probe unit is coupled directly to a vibrator unit through an engaging hole portion if the probe unit is combined with a proper sheath. If the probe unit is combined with an improper sheath, the engaging portion is not allowed to pass through the engaging hole portion. Thus, the probe unit and the vibrator unit can be prevented from being wrongly assembled, and only those parts which wear easily can be replaced. And the same protection system can be applied to an engagement of a sheath unit and a body of ultrasonic surgical instrument.

5 Claims, 25 Drawing Sheets

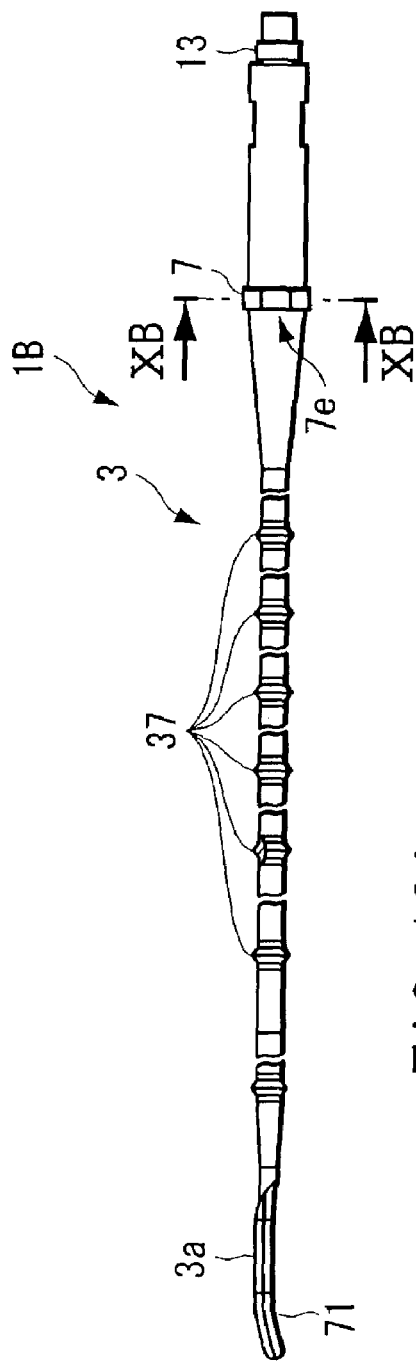
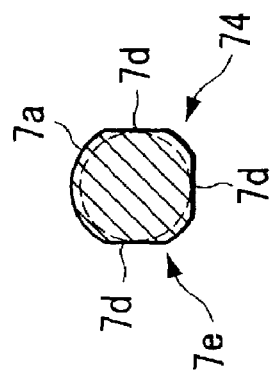
FIG. 10A
FIG. 10B

ULTRASONIC SURGICAL INSTRUMENT

CROSS-REFERENCE TO RELATED APPLICATIONS

This application is based upon and claims the benefit of priority from the prior Japanese Patent Applications No. 2002-005103, filed Jan. 11, 2002; and No. 2002-355608, filed Dec. 6, 2002, the entire contents of both of which are incorporated herein by reference.

BACKGROUND OF THE INVENTION

1. Field of the Invention

The present invention relates to an ultrasonic surgical instrument capable of incising, ablating, or coagulating organic tissues by utilizing ultrasonic waves.

2. Description of the Related Art

As an ultrasonic surgical instrument for incising, ablating, or coagulating organic tissues by utilizing ultrasonic waves, in general, there is an apparatus that is described in Jpn. Pat. Appln. KOKAI Publications Nos. 9-98979, 10-5236, etc. This ultrasonic surgical instrument comprises an elongated insertion section that can be inserted into a patient's body. A sheath portion of the insertion section is provided with a mantle tube. A control section on the hand side is coupled to the proximal end portion of the insertion section. The control section is furnished with an ultrasonic vibrator for generating ultrasonic vibration. An operating section for treating organic tissues is provided on the distal end portion of the insertion section. The operating section is provided with an ultrasonic probe.

A substantially shaft-shaped vibration transmitting member is passed through the mantle tube. The proximal end portion of the vibration transmitting member is detachably connected to the ultrasonic vibrator by means of a screw-type junction. Ultrasonic vibration generated by the vibrator is transmitted to the ultrasonic probe of the operating section by means of the vibration transmitting member.

Further, the operating section is provided with a jaw that faces the ultrasonic probe. The jaw is rockably supported on the distal end portion of the insert section. A holding member portion of the jaw that touches an organic tissue is formed of a resin material such as polytetrafluoroethylene.

A control rod for driving the jaw is fitted in the mantle tube for axial movement. The distal end portion of the rod is coupled to the jaw of the operating section. The operating section is provided with a control handle. This handle is coupled to the proximal end portion of the rod.

As the control handle is operated, the control rod is advanced or retreated in the axial direction. As the rod is moved in this manner, the jaw is opened or closed with respect to the ultrasonic probe. If the jaw is closed, the organic tissue is held between the probe and the jaw. Then, the ultrasonic vibrator is driven in this state. As this is done, ultrasonic vibration from the vibrator is transmitted to the ultrasonic probe by means of the vibration transmitting member. Thus, the organic tissue between the probe and the jaw can be incised, ablated, or coagulated by utilizing ultrasonic waves.

Recently, there has been a demand for the proper use of an appropriate ultrasonic surgical instrument according to the region to be treated and the method of treatment. In this case, the distal end portion of the ultrasonic surgical instrument is expected to have an optimum shape for the region to be treated and the method of treatment. To meet this requirement, a set of ultrasonic surgical instruments of a plurality of types having different tip shapes is completed in advance, and the surgical instruments are used alternatively and properly according to the region to be treated and the method of treatment.

In many surgical instruments for endoscopic surgical operations, parts other than the distal end portion are common to a plurality of types of instruments. A reusable ultrasonic surgical instrument, in particular, can be disassembled into a plurality of units to facilitate cleaning. For example, it can be disassembled into three units, including a sheath unit that has a sheath or a mantle tube of an insertion section and a handle of a control section joined together, a vibrator unit having a vibrator, and a probe unit having a probe.

In order to use an ultrasonic surgical instrument having an optimum shape according to the region to be treated and the method of treatment during an endoscopic surgical operation, the probe unit or sheath unit to be joined to the body of the surgical instrument currently in use must be replaced with a new one when the region or method is changed. In replacing the probe unit, in this case, the probe unit and the sheath unit for proper use must be selected and reassembled after the instrument body is disassembled.

In many surgical instruments for endoscopic surgical operations, however, the insertion section is formed having a small outside diameter to ensure low invasion. Correspondingly, the distal end portion of the insertion section is thin and small. Therefore, it is hard apparently to discriminate the difference in the tip shape. In reassembling the disassembled body of the ultrasonic surgical instrument, therefore, the probe unit and the sheath unit cannot be selected and combined properly. Thus, there is a possibility of the probe unit and the sheath unit being assembled in a wrong combination. Although this mistake should be noticed during operation, in this case, the probe unit and the sheath unit must be joined in a proper combination. Thus, reassembling the ultrasonic surgical instrument body requires extra operating time and results in impeding the surgical operation. If the units are used in a wrong combination, moreover, they cannot fulfill their desired function.

BRIEF SUMMARY OF THE INVENTION

The present invention has been contrived in consideration of these circumstances, and its object is to provide an ultrasonic surgical instrument designed so that a probe can be prevented from being joined in a wrong combination during assembly and can be properly used according to the region to be treated and the method of treatment, and that high-durability parts other than worn parts can continue to be used without being replaced with new ones if only those parts which wear easily are replaced, thus ensuring the lower cost of surgical operations.

According to an aspect of the invention, there is provided an ultrasonic surgical instrument comprising: a common unit formed usable in common in a plurality of types of instruments; and a plurality of individual unit including dedicated parts capable of being alternatively joined together with the common part to form an ultrasonic surgical instrument assembly, the individual units including incompatible joining preventing portions located at the junctions with the other individual units and capable of preventing different types of instruments from being joined together.

As the individual units are coupled to one another, according to the invention, the incompatible joining preventing portions prevent individual units of different types from being joined together.

In the ultrasonic surgical instrument according to one embodiment of the present application, the one individual unit is formed of a probe unit having a probe tip capable of transmitting ultrasonic vibration, the other individual unit is formed of a sheath unit including a sheath having a passage through which the probe unit can pass, and the incompatible joining preventing portions are probe insertion preventing portions adapted to allow the insertion of only the probe unit of the same instrument type and prevent the insertion of the probe unit of a different type when the probe unit passes through the passage of the sheath unit.

When the probe unit and the sheath unit are coupled to each other, according to the invention, the proximal end portion of the probe is kept so as to be able to pass through the probe insertion preventing portions to the vibrator side in the case where the sheath and the probe for the same instrument type are combined properly. In the case where the sheath and the probe for different instrument types are combined improperly, the probe insertion preventing portions prevent the proximal end portion of the probe from passing to the vibrator side.

In the ultrasonic surgical instrument according to an embodiment of the present application, the probe unit insertion preventing portions have fitting portions in a part of the passage of the sheath unit, the respective sectional shapes of the fitting portions are exclusive depending on the instrument type.

When the probe unit and the sheath unit are coupled to each other, according to the invention, the proximal end portion of the probe is kept so as to be able to pass through the probe insertion preventing portions having corresponding sectional shapes to the vibrator side in the case where the sheath and the probe for the same instrument type are combined properly. In the case where the sheath and the probe for different instrument types are combined improperly, the probe insertion preventing portions having different sectional shapes prevent the proximal end portion of the probe from passing to the vibrator side.

In the ultrasonic surgical instrument according to another embodiment of the present application, the fitting portions are located corresponding to vibration nodes of the probe unit.

Since the fitting portions are located corresponding to the vibration nodes of the probe at which vibration is suppressed when the probe is driven, according to the invention, noise can be prevented from being produced at the junction between the probe unit and the sheath unit.

In the ultrasonic surgical instrument in which a plurality of component units are joined together to form an ultrasonic surgical instrument assembly so as to be able to be disassembled comprising:

the component units including a common unit formed of a common part usable in common in a plurality of types of instruments and a plurality of individual units including dedicated parts capable of being alternatively used for each instrument type, the one individual unit being formed of a probe unit having a probe tip capable of transmitting ultrasonic vibration, the other individual unit being formed of a sheath unit including a sheath formed having a passage through which the probe unit can be passed, the sheath unit is composed of a tip unit including the sheath and a control section unit on the proximal end portion of the sheath joined so as to be able to be disassembled, and a junction between the tip unit and the control section unit having an incompatible joining preventing portion for preventing the different types of tools from being joined to one another.

When the tip unit and the control section unit are coupled to each other, according to the invention, the proximal end portion of the tip unit is kept so as to be able to pass through the incompatible joining preventing portion to the side of the control section unit in the case where the tip unit and the control section unit for the same instrument type are combined properly. In the case where the tip unit and the control section unit for different instrument types are combined improperly, the incompatible joining preventing portion prevents the proximal end portion of the tip unit from passing to the side of the control section unit.

In the ultrasonic surgical instrument comprising:
a probe capable of transmitting ultrasonic vibration;
a sheath designed for use in combination with the probe, having a passage through which the probe can pass and including female fittings which have a hole communicating with the passage;
engaging portions which are provided on the probe and fitted in the female fittings of the sheath; and
probe insertion preventing portions which are provided on the female fittings and which abut on the engaging portions to prevent the engaging portions from being fitted into the female fittings, which the probe is inserted into the passage and is not used in combination with the sheath.

In the ultrasonic surgical instrument comprising:
a probe capable of transmitting ultrasonic vibration;
a sheath designed for use in combination with the probe and having a passage through which the probe can pass;
an instrument body designed for use in combination with the sheath;
engaging portions provided on the probe which is used in combination with the sheath; and
female fittings which are provided on the instrument body and which abut on the engaging portions not to hold the engaging portions, when the prove is not used in combination with the sheath.

In the ultrasonic surgical instrument comprising:
a probe capable of transmitting ultrasonic vibration;
a sheath designed for use in combination with the probe and having a passage through which the probe can pass;
an instrument body designed for use in combination with the sheath;
a sheath unit incorporated in the sheath and selectively connected to the instrument body;
female fittings provided on the instrument body; and
a sheath unit connecting portion provided on the sheath unit, held in the female fittings when the instrument body is used in combination with the sheath, and abutting on the female fittings when the instrument body is not used in combination with the sheath.

According to the present invention, the probe can be prevented from being joined in a wrong combination during assembly and can be properly used according to the region to be treated and the method of treatment. If only those parts which wear easily are replaced, moreover, high-durability parts other than the worn parts can continue to be used without being replaced with new ones. Thus, the cost of surgical operations can be lowered.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL
VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 10A is a side view showing a probe unit of the second ultrasonic surgical instrument of the first embodiment;

FIG. 10B is a sectional view taken along line XB—XB of FIG. 10A;

Figure 31:
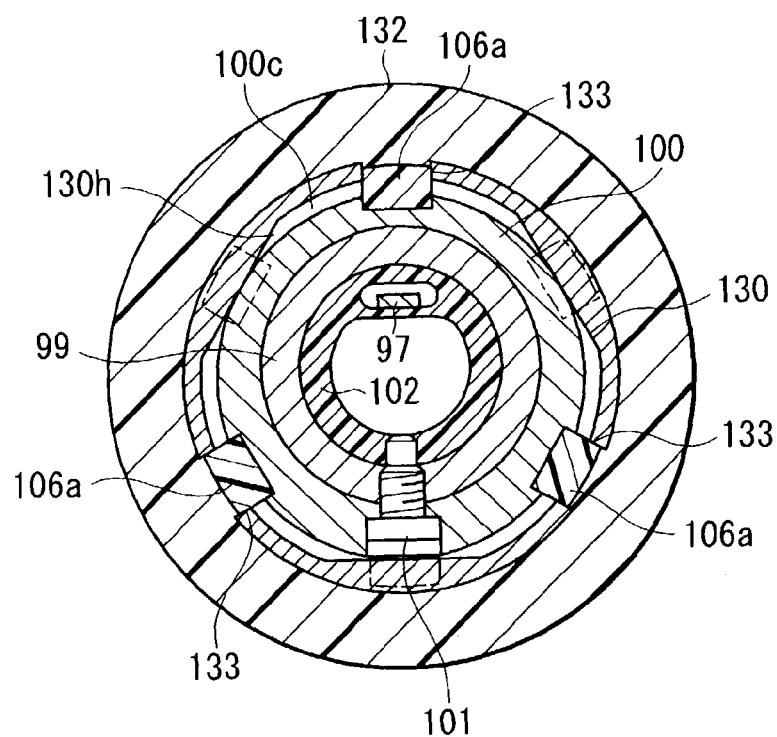
Figure 32:
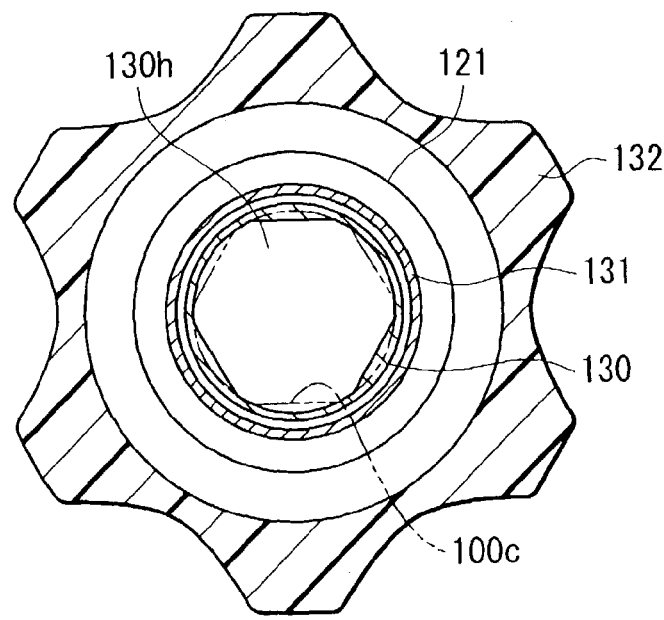

FIG. 31 is a cross-sectional view showing the way of engagement of engaging claws of a detent with the tip unit and the control section unit of the ultrasonic surgical instrument of the second embodiment joined entirely; and FIG. 32 is a cross-sectional view showing the way of engagement of a flange of a control section connecting member and an engaging hole portion of a tip unit connecting member of the ultrasonic surgical instrument of the second embodiment.

DETAILED DESCRIPTION OF THE INVENTION

A first embodiment of the present invention will now be described with reference to FIGS. 1 to 13. According to the present embodiment, there is provided an ultrasonic surgical instrument system, which includes ultrasonic surgical instruments of a plurality of types having different tip shapes. A set of these instruments is completed in advance in carrying out ultrasonic treatment such as incision, ablation, or coagulation of organic tissues by utilizing ultrasonic waves. In this system, the surgical instruments are properly used according to the region to be treated and the method of treatment.

According to this system, a first ultrasonic surgical instrument 1A shown in FIGS. 1 to 7B and a second ultrasonic surgical instrument 1B shown in FIGS. 8A to 12B are prepared in advance. The first and second ultrasonic surgical instruments 1A and 1B are properly used according to the region to be treated and the method of treatment.

Figure 1:
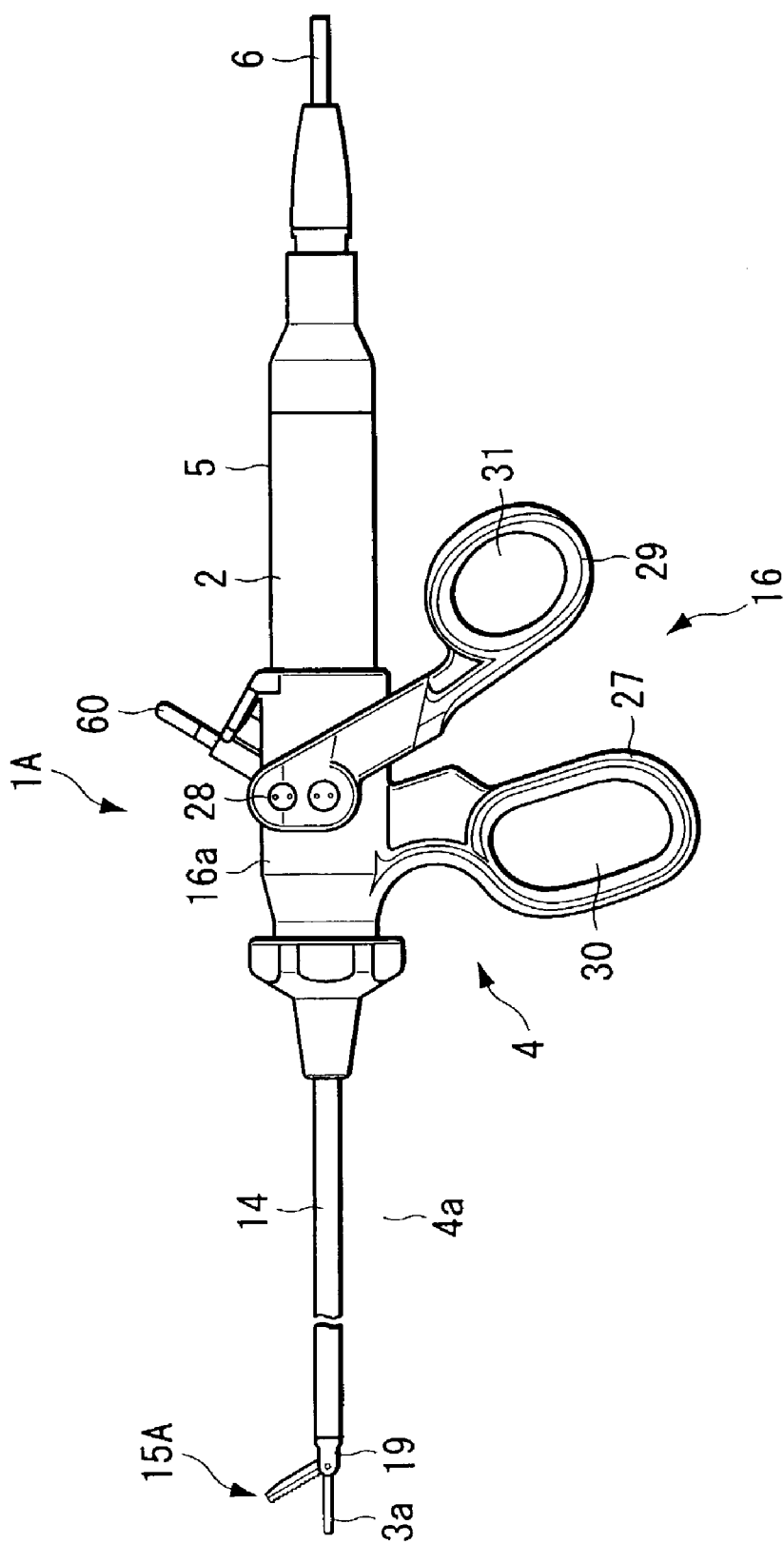
FIG. 1 is a side view showing a general assembled state of an ultrasonic surgical instrument according to a first embodiment of the invention.

FIG. 1 shows the first ultrasonic surgical instrument 1A of the present embodiment. In this surgical instrument 1A, three component units 2, 3 and 4 are joined together to form an ultrasonic surgical instrument assembly in a manner such that they can be disassembled. One of the component units is formed of a vibrator unit (common unit) 2 that can be used in common in a plurality of instrument types. Two other component units include a probe unit (individual unit) 3, which is alternatively used for each instrument type, and a sheath unit (individual unit) 4. The vibrator unit 2, probe unit 3, and sheath unit 4 are joined so as to be detachable from one another.

A vibrator is incorporated in the vibrator unit 2. The vibrator generates ultrasonic vibration by means of a piezoelectric element (not shown) that converts current into ultrasonic vibration. The outside of the piezoelectric element is enwrapped in a cylindrical vibrator cover 5. Further, a cord 6 extends from the rear end of the vibrator unit 2. It serves to supply current for generating ultrasonic vibration from a power source unit body (not shown).

Figure 2:
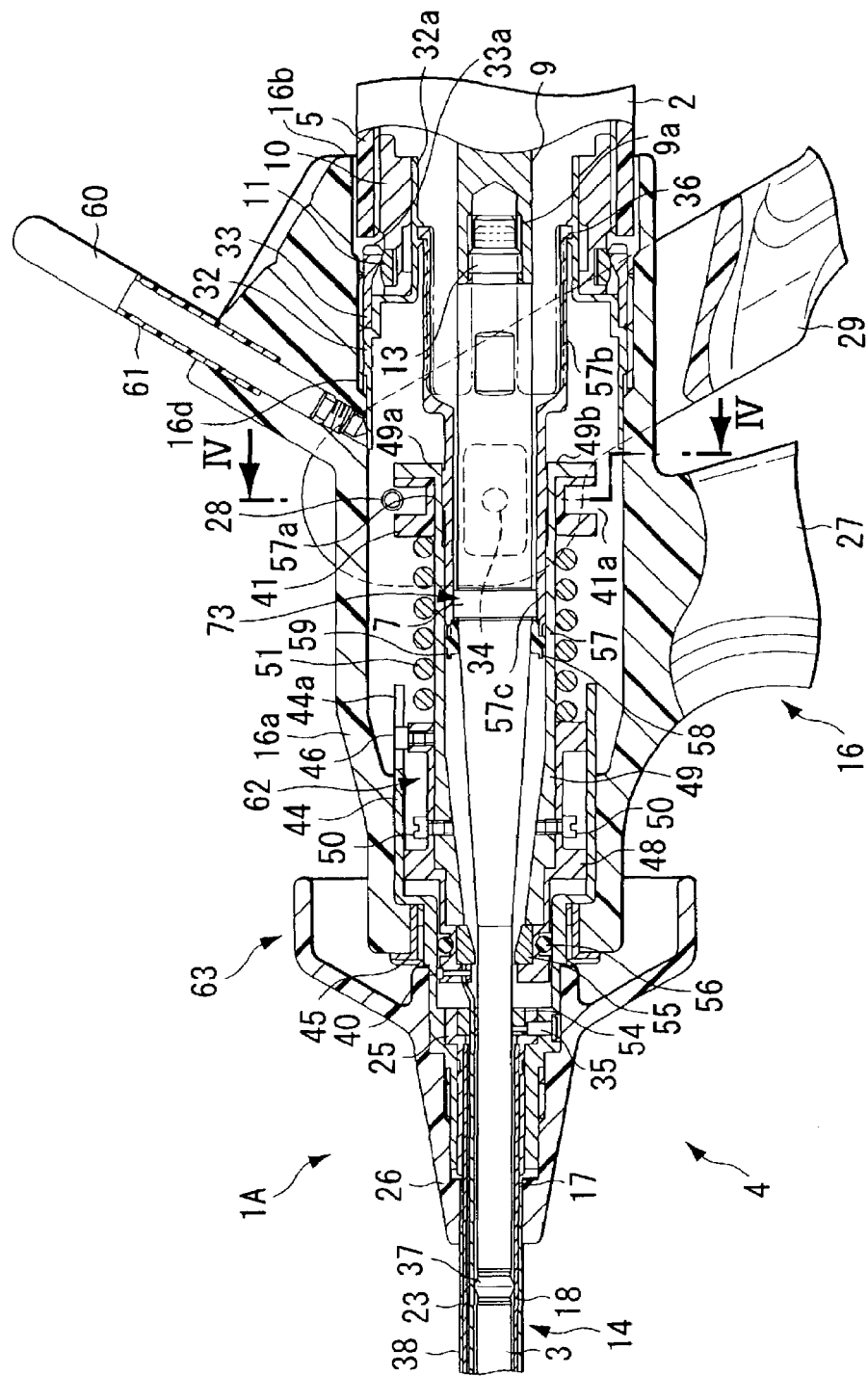
FIG. 2 is a longitudinal sectional view showing the internal construction of a control section of the ultrasonic surgical instrument of the first embodiment.

As shown in FIG. 2, moreover, an attachment 10 for unit connection is fixed to the front end of the vibrator unit 2. The attachment 10 is fitted with a metallic C-ring 11, which is formed by partially cutting a ring and has the shape of a C. The attachment 10 can be detachably coupled to the sheath unit 4.

Further, the proximal end portion of a horn 9 for increasing the amplitude of ultrasonic vibration is coupled to the front end portion of the ultrasonic vibrator (not shown) in the vibrator cover 5. A tapped hole portion 9a for probe attachment is formed in the distal end portion of the horn 9.

Figure 5A:
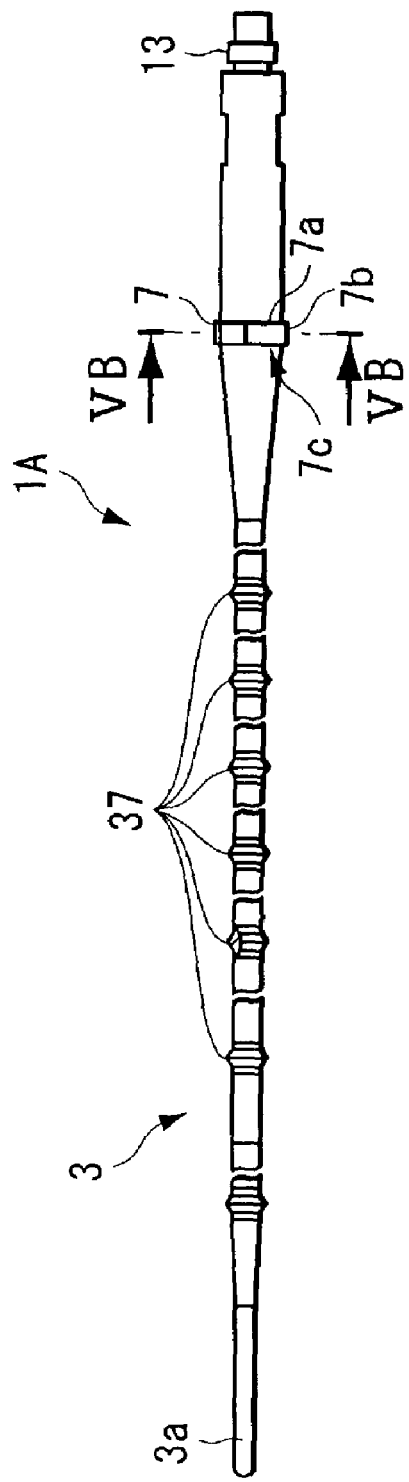
FIG. 5A is a side view showing a probe unit of the first ultrasonic surgical instrument of the first embodiment.

FIG. 5A shows an external appearance of the whole probe unit 3. The probe unit 3 is designed so that its overall length is an integral multiple of the half-wavelength of ultrasonic vibration. The proximal end portion of the probe unit 3 is provided with a threaded portion 13 for threaded engagement with the tapped hole portion 9a of the horn 9. The thread portion 13 is screwed into the tapped hole portion 9a of the horn 9 of the vibrator unit 2. Thus, the probe unit 3 and the vibrator unit 2 are joined together.

Further, a straight probe tip 3a is provided on the distal end portion of the probe unit 3. In order to obtain the necessary amplitude for treatment at the probe tip 3a, moreover, the axial cross section of the probe unit 3 is reduced at several vibration nodes in the middle of its axis. Elastic rubber rings 37 are attached to the probe unit 3 in several vibration node positions in the middle of its axis. The rubber rings 37 can prevent the probe unit 3 and the sheath unit 4 from interfering with each other.

Figure 5B:
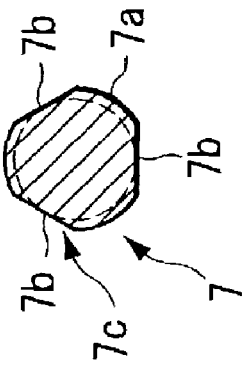
FIG. 5B is a sectional view taken along line VB—VB of FIG. 5A.

Furthermore, a flange portion 7 of, for example, a metallic material is provided on the probe unit 3 in the vibration node position on the extreme proximal end side with respect to the axial direction of the probe unit 3. As shown in FIG. 5B, a noncircular engaging portion (fitting portion) 7c is formed on the outer peripheral surface of the flange portion 7. The engaging portion 7c is formed having several flat portions 7b (three in number according to the present embodiment) that are obtained by cutting several (or three) spots of a circular outer peripheral portion 7a of the flange portion 7. The engaging portion 7c has a substantially triangular sectional shape. The cross section of the noncircular engaging portion 7c need not always be substantially triangular, and may alternatively be in various other noncircular shapes. However, the sectional shape of the engaging portion 7c should be proper to the instrument type, and is expected to prevent engagement with instruments of any other types.

Figure 3A:
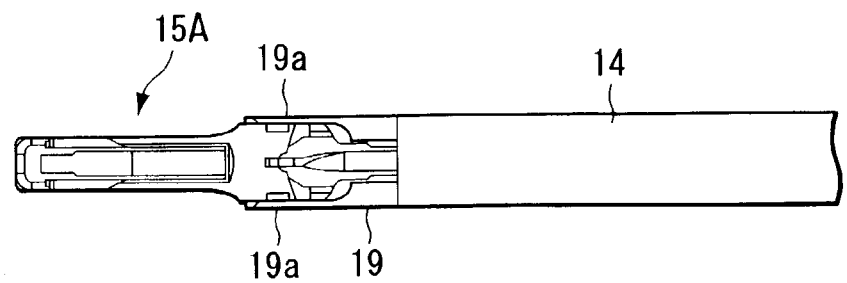
FIG. 3A is a plan view showing a distal operating section of a first ultrasonic surgical instrument of the first embodiment.

The sheath unit 4 is provided with an elongated insertion section 4a and a control section 16. The insertion section 4a can be inserted into a patient's body cavity that undergoes a surgical operation. The control section 16 is coupled to the proximal end portion of the insertion section 4a. Further, a jaw (operating section component) 15 as a distal working section for holding an organic tissue is provided on the distal end of the insertion section 4a. As shown in FIG. 3A, the jaw 15 has a substantially straight shape corresponding to the straight probe tip 3a of the probe unit 3.

Figure 6:
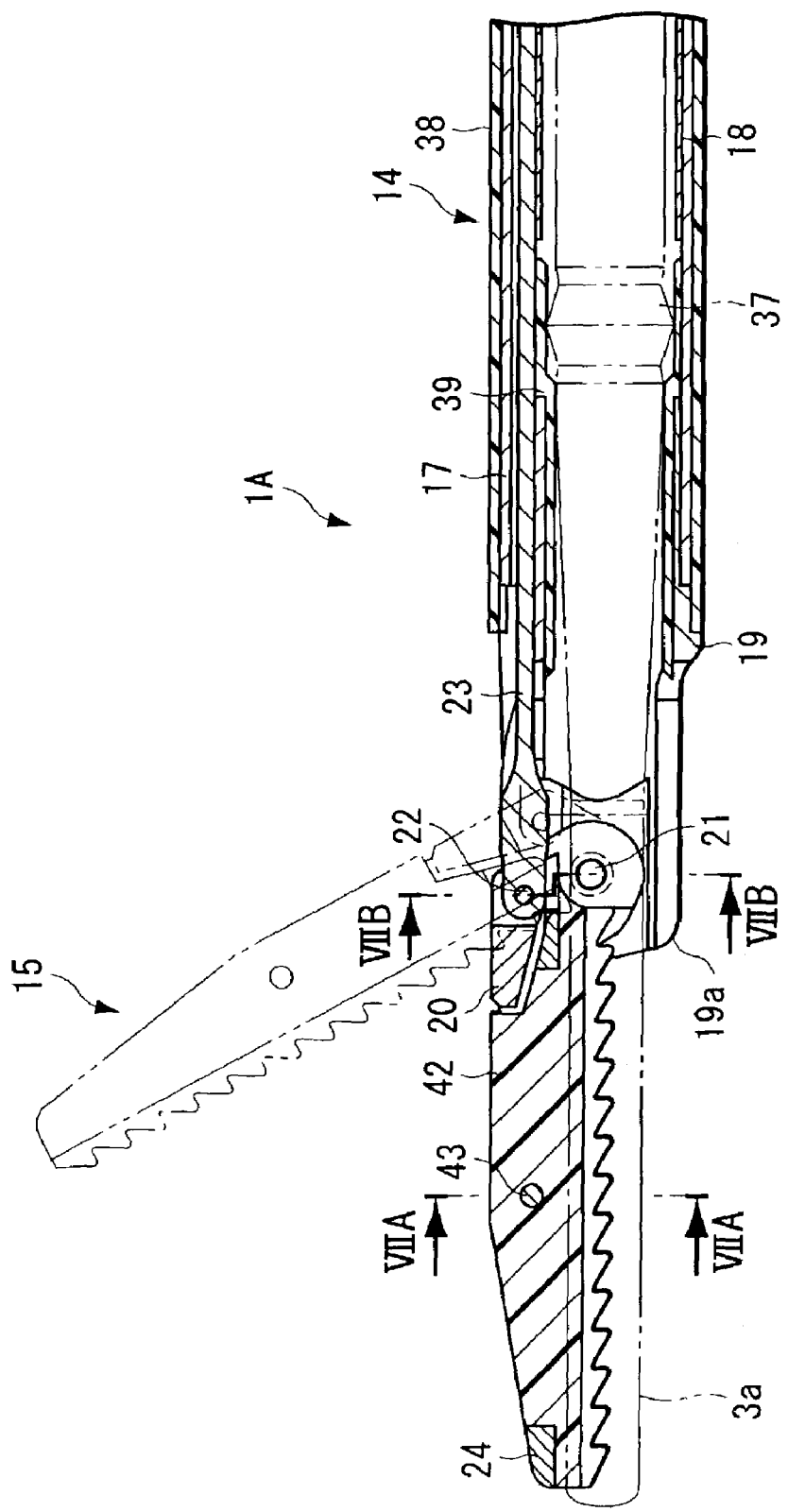
FIG. 6 is a longitudinal sectional view of the distal operating section of the first ultrasonic surgical instrument of the first embodiment.

As shown in FIG. 6, moreover, the insertion section 4a is provided with a sheath 14, which is composed of an outer pipe 17 and an inner pipe 18 inside the pipe 17. An insulating tube 38 covers the outside of the outer pipe 17. A channel through which the probe unit 3 is to be passed is formed inside the inner pipe 18. Further, a channel for the passage of a drive shaft 23 (mentioned later) is formed between the outer and inner pipes 17 and 18.

The proximal end portion of a substantially cylindrical tip cover 19 is fixed to the distal end portion of the outer pipe 17. A pipe-shaped presser member 39 is attached to the inner peripheral surface side of the proximal end portion of the tip cover 19. The presser member 39 presses the probe unit 3 to prevent it touching the tip cover 19.

At the distal end portion of the tip cover 19, as shown in FIG. 3A, moreover, a pair of jaw supporting portions 19a, left and right, extend forward from the outer pipe 17. As shown in FIG. 7B, a jaw body 20 is rockably mounted on the jaw supporting portions 19a by means of two pivot pins 21.

Figure 7A:
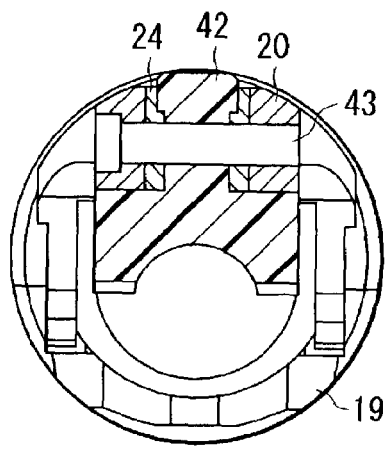
FIG. 7A is a sectional view taken along line VIIA—VIIA of FIG. 6.
Figure 7B:
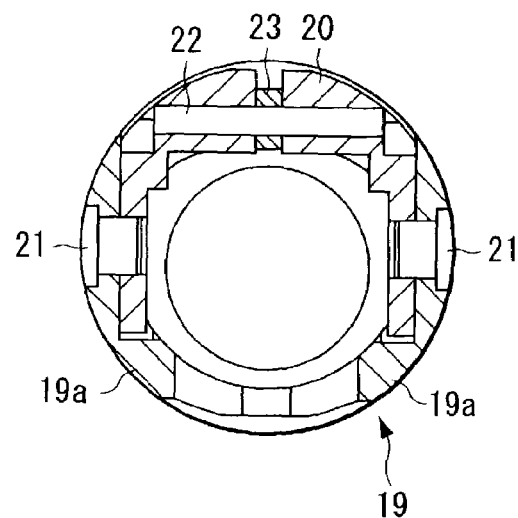
FIG. 7B is a sectional view taken along line VIIB—VIIB of FIG. 6.

As shown in FIG. 7A, furthermore, a holding member 42 formed of a resin such as PTFE and a holding portion mounting member 24 for holding the holding member 42 are mounted on the jaw body 20 by means of a pin 43 so as to be rockable through a fixed angle. As shown in FIG. 7B, moreover, the distal end portion of the drive shaft 23 is coupled to the rear end of the jaw body 20 by means of a pin 22. As shown in FIG. 6, the drive shaft 23 passes through the tip cover 19 and then between the outer and inner pipes 17 and 18 of the sheath 14, and extends to the side of the control section 16.

Figure 4:
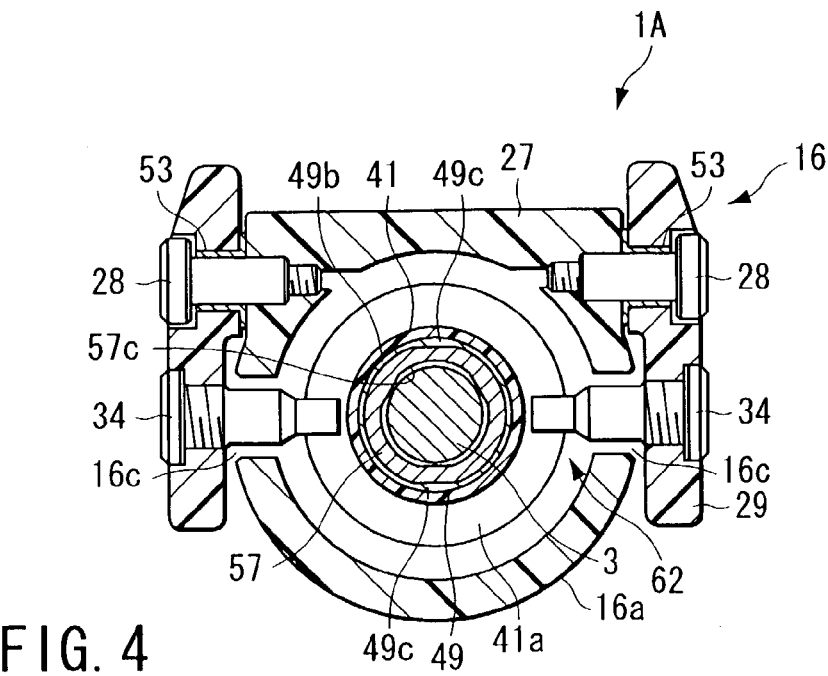
FIG. 4 is a sectional view taken along line IV—IV of FIG. 2.

As shown in FIG. 4, moreover, the control section 16 is provided with a substantially cylindrical control section housing 16a. A vibrator connecting portion 16b is formed on the proximal end portion of the housing 16a.

A stationary handle 27 and a movable handle 29 are provided on the outer peripheral surface of the control section housing 16a. The upper part of the stationary handle 27 is molded integrally with the cylindrical housing 16a.

As shown in FIG. 4, furthermore, pivot pins 28 are located individually on the opposite side faces of the upper end portion of the stationary handle 27. The upper end portion of the movable handle 29 is rockably mounted on the upper end portion of the stationary handle 27 by means of the pivot pins 28. Further, bushes 53 formed of low-friction PTFE or the like for better sliding performance are arranged on the pivot pins 28, individually.

Finger loops 30 and 31 are attached to the lower end portions of the stationary and movable handles 27 and 29, respectively. As the handles are gripped with fingers in the loops, the movable handle 29 rocks around the pivot pins 28.

Thus, the movable handle 29 can be swung open and closed with respect to the stationary handle 27.

Further, working pins 34 for operating force transmission protrude inward from those regions of the movable handle 29 which are situated near the pivot pins 28, individually. The control section housing 16a is formed having windows 16c for the passage of the working pins 34. Each working pin 34 of the movable handle 29 extends into the control section housing 16a through its corresponding window 16c of the housing 16a.

An operating force transmitting mechanism 62 for transmitting the operating force of the movable handle 29 to the drive shaft 23 is located in the control section housing 16a. The transmitting mechanism 62 is provided with a substantially cylindrical slider receiving member 49. A substantially cylindrical driving force transmitting intermediate member 48 is located on the distal end side of the outer peripheral surface of the receiving member 49. The intermediate member 48 is attached to the receiving member 49 by means of pins 50. Further, the proximal end portion of the drive shaft 23 is coupled to the distal end portion of the intermediate member 48 by means of a driving force transmitting pin 40.

A flange-shaped stopper portion 49a outwardly extends from the proximal end edge portion of the slider receiving member 49 substantially at right angles thereto. A substantially ring-shaped slider member 41 is mounted for axial sliding motion on the proximal end side of the outer peripheral surface of the receiving member 49. Further, a coil spring 51 is fitted on the outer peripheral surface of the receiving member 49 so as to be interposed between the driving force transmitting intermediate member 48 and the slider member 41 with a fixed urging force.

A ring-shaped engaging groove 41a is formed on the outer peripheral surface of the slider member 41 so as to extend in the circumferential direction. As shown in FIG. 4, the working pins 34 of the movable handle 29 are fitted in the engaging groove 41a. If the movable handle 29 is caught and swung relatively to the stationary handle 27, the working pins 34 rock around the pivot pins 28 as the movable handle 29 rocks. Thereupon, the slider member 41 that is in engagement with the pins 34 advances or retreats in the axial direction. Further, the driving force transmitting intermediate member 48 that is coupled to the slider member 41 by means of the coil spring 51 also moves, whereupon the driving force transmitting pin 40 causes the drive shaft 23 to move. Thus, the jaw body 20 of the jaw 15 rocks around the pivot pins 21.

As the organic tissue is held between the holding member 42 of the jaw 15 and the probe tip 3a of the probe unit 3 by this operation, moreover, the holding member 42 rocks through the fixed angle around the pin 43, following the deflection of the probe tip 3a. Thus, force uniformly acts the holding member 42 throughout its length. If ultrasonic waves are output in this state, the organic tissue, e.g., a blood vessel, can be coagulated or incised.

The sheath unit 4 according to the present embodiment is provided with a rotating mechanism 63, which drives the jaw 15 and the probe unit 3 at the distal end portion of the first ultrasonic surgical instrument 1A to rotate around the axis. The mechanism 63 is provided with a cylindrical pipe fixing member 25 that is located in the control section 16. The proximal end portion of the outer pipe 17 of the sheath 14 is fixed to the inner peripheral surface of the member 25. A link member 44 is fixed to the pipe fixing member 25 by means of a fixing pin 35.

A rotating knob 26 that is located in front of the control section housing 16a is mounted on the distal end side of the link member 44. A guide groove 44a is formed in the rear end portion of the link member 44 so as to extend in the axial direction of the probe unit 3. A pin 46 that protrudes form the rear end portion of the driving force transmitting intermediate member 48 is fitted in the guide groove 44a. Thus, the intermediate member 48 is coupled to the link member 44 by means of the pin 46 for integral rotation around the axis.

Further, a fixing ring 45 that is rotatably coupled to the front end portion of the control section housing 16a is fixed to the middle portion of the link member 44. Thus, the pipe fixing member 25, along with the link member 44, is attached to the control section housing 16a by means of the fixing ring 45 so as to be rotatable around the axis with respect to the control section housing 16a.

The driving force transmitting intermediate member 48 is fitted with packing 56 to prevent pneumoperitoneum gas or the like from leaking out of the distal end of the sheath 14 through an inside gap during laparoscopy. Further, high-frequency connecting pins 54 and 55 formed of low-friction PTFE are arranged individually on the inner peripheral surface side of the rear end portion of the pipe fixing member 25 and the inner peripheral surface side of the intermediate member 48 to prevent the probe unit 3 directly touching the members.

Further, a backwardly leaning high-frequency connecting pin 60 is attached to the rear end portion of the control section housing 16a. An active cord (not shown) for supplying high-frequency current from a high-frequency cautery power source unit (not shown) is connected to the connecting pin 60. Furthermore, an insulating cover 61 for securing the electrical safety of the pin 60 having the active cord thereon is attached to the proximal end portion of the pin 60.

A tapped hole 16d is formed in the rear end portion of the control section housing 16a. A ring-shaped connecting member 32 for electrical connection and a connecting ring 33 for connection to the vibrator unit 2 are screwed in the tapped hole 16d. The distal end portion of the connecting member 32 is connected electrically to the proximal end portion of the high-frequency connecting pin 60.

Further, the rear end portion of the connecting member 32 is formed having a small-diameter connecting cylinder portion 32a that can be inserted into the attachment 10 of the vibrator unit 2. A vibrator unit engaging groove is formed between the connecting cylinder portion 32a of the connecting member 32 and the connecting ring 33. The rear end portion of the connecting ring 33 is formed having an engaging protuberance 33a, which is smaller in diameter than the C-ring 11 of the attachment 10 of the vibrator unit 2. When the sheath unit 4 and the vibrator unit 2 are coupled to each other, the attachment 10 of the vibrator unit 2 can be removably inserted into the vibrator unit engaging groove between the connecting cylinder portion 32a of the connecting member 32 and the connecting ring 33. As the C-ring 11 is elastically deformed to get over the engaging protuberance 33a of the connecting ring 33, in this state, the sheath unit 4 and the vibrator unit 2 are caused to detachably engage each other.

An engaging hole portion 49b having a noncircular or irregular shape is formed on the proximal end side of the slider receiving member 49. Flat portions 49c are formed on two opposite parts of the hole portion 49b.

The distal end side of a substantially cylindrical contact member (tubular member) 57 formed of a conductive material, e.g., a metallic material, is inserted into the engaging hole portion 49b of the slider receiving member 49. An external shape portion 57a corresponding to the shaped engaging hole portion 49b in shape is formed on the distal end portion of the contact member 57. As the external shape portion 57a of the contact member 57 and the engaging hole portion 49b of the receiving member 49 engage each other, the two members are fixedly coupled to each other without the possibility of relative rotation.

A slit-shaped large-diameter portion 57b having a diameter larger than that of the slider receiving member 49 is formed on the rear end portion of the contact member 57. An outwardly bent projection 36 protrudes from the outer periphery of the rear end portion of the large-diameter portion 57b. The outside diameter of the projection 36 is greater than the inside diameter of the connecting cylinder portion 32a of the connecting member 32. The projection 36 on the rear end side of the contact member 57 is pressed against the inner peripheral surface side of the cylinder portion 32a in a manner such that it is elastically deformed by the slit structure of the large-diameter portion 57b.

A connecting rubber ring 58 formed of conductive rubber is attached to the distal end side of the contact member 57. When the probe unit 3 and the sheath unit 4 are coupled together, the rubber ring 58 on the contact member 57 is pressed against the probe unit 3 in a position near a vibration node of the probe unit 3. Thus, the rubber ring 58 and the probe unit 3 can be connected electrically to each other with reliability.

Further, a protrusion 59 protrudes outward from the outer peripheral surface of the rubber ring 58 outside the contact member 57. The protrusion 59 is pressed against the inner peripheral surface of the slider receiving member 49 so that it serves as packing for preventing pneumoperitoneum gas or the like from leaking out through the internal gap of the receiving member 49 during laparoscopy.

A substantially triangular engaging hole portion (fitting portion) 57c is formed in the inner peripheral surface of the distal end portion of the contact member 57. The engaging portion 7c of the flange portion 7 of the probe unit 3 can pass through the hole portion 57c. The hole portion 57c has the same shape with the engaging portion 7c of the flange portion 7, that is, a substantially triangular sectional shape. More specifically, the hole portion 57c is formed having three flat portions 7b that are obtained by cutting three spots of the circular outer peripheral portion 7a, as shown in FIG. 5B. The cross section of the noncircular engaging hole portion 57c need not always be substantially triangular, and may alternatively be in various other noncircular shapes. However, the sectional shape of the hole portion 57c should be proper to the instrument type, and is expected to prevent engagement with instruments of any other types.

When the probe unit 3 and the sheath unit 4 are joined together, the substantially triangular engaging hole portion 57c of the contact member 57 and the substantially triangular engaging portion 7c of the flange portion 7 are in engagement with each other, as shown in FIG. 2. The engaging hole portion 57c and the engaging portion 7c in engagement with each other form a probe insertion preventing portion (incompatible joining preventing portion) 73 when the probe unit 3 is passed through a passage of the sheath unit 4. The preventing portion 73 allows insertion of the probe unit 3 of instruments of the same type only and prevents insertion of the probe unit 3 of instruments of different types.

The rotating mechanism 63 of the present embodiment is driven by means of the rotating knob 26. As the knob 26 is rotated, the contact member 57 and the probe unit 3 are slid in the direction of rotation around the axis by means of the link member 44, driving force transmitting intermediate member 48, and slider receiving member 49 in succession. As the link member 44 rotates, moreover, the sheath 14 is rotated around the axis by means of the pipe fixing member 25. Thereupon, the jaw 15 at the distal end portion of the first ultrasonic surgical instrument 1A is rotated together with the sheath 14 around the axis.

Also while the rotating knob 26 is rotating, the projection 36 of the large-diameter portion 57b of the contact member 57 is always kept in contact with the connecting member 32 by means of elastic force and connected electrically to the member 32. Accordingly, the high-frequency connecting pin 60 is kept connected electrically to the probe unit 3 by means of the connecting member 32, contact member 57, and rubber ring 58. Thus, the organic tissue can be treated with high-frequency current that is supplied through the distal end portion of the probe unit 3.

The second ultrasonic surgical instrument 1B, like the first ultrasonic surgical instrument 1A, comprises three units, the vibrator unit 2, probe unit 3, and sheath unit 4. The second instrument 1B differs from the first instrument 1A in the respective shapes of the probe tip 3a of the probe unit 3, flange portion 7 of the probe unit 3, jaw 15 on the distal end of the sheath unit 4, etc., in the following manner.

As shown in FIG. 10A, the probe tip 3a at the distal end portion of the probe unit 3 of the second ultrasonic surgical instrument 1B is provided with a shaped portion (engaging portion) 71. The shaped portion 71 has a nonsymmetrical shape, e.g., a substantially arcuate shape (curved shape), which is bent away from the axial direction. Further, the flange portion 7 of the probe unit 3 is formed having three flat portions 7d that are obtained by cutting three spots of the circular outer peripheral portion 7a of the flange portion 7. Thus, the flange portion 7 has an engaging portion (fitting portion) 7e with a substantially square cross section. The cross section of the noncircular shaped portion 74 need not always be substantially square, and may alternatively be in various other noncircular shapes. However, the sectional shape of the shaped portion 74 should be proper to the instrument type, and is expected to prevent engagement with instruments of any other types.

The jaw 15, different in shape form that of the first ultrasonic surgical instrument 1A, is provided on the distal end of the sheath unit 4 of the second ultrasonic surgical instrument 1B. The jaw 15 is formed having a substantially arcuate shaped portion 72, which corresponds to the shaped portion 71 of the probe tip 3a of the probe unit 3 in shape.

Further, an engaging hole portion (fitting portion) 57d is formed on the inner peripheral surface of the distal end portion of the contact member 57 in the control section housing 16a of the sheath unit 4. The engaging portion 7e of the flange portion 7 of the probe unit 3 can pass through the hole portion 57d. The hole portion 57d has the same shape as the engaging portion 7e of the flange portion 7, that is, a substantially square sectional shape. More specifically, the hole portion 57d is formed having three flat portions 7d that are obtained by cutting three spots of the circular outer peripheral portion 7a, as shown in FIG. 10B.

When the probe unit 3 and the sheath unit 4 are joined together, also in the second ultrasonic surgical instrument 1B, the substantially square engaging hole portion 57d of the contact member 57 and the substantially square engaging portion 7e of the flange portion 7 are in engagement with each other. The engaging hole portion 57d and the engaging portion 7e in engagement with each other form a probe insertion preventing portion (incompatible joining preventing portion) 74 when the probe unit 3 is passed through the passage of the sheath unit 4. The preventing portion 74 allows insertion of the probe unit 3 of instruments of the same type only and prevents insertion of the probe unit 3 of instruments of different types.

The first and second ultrasonic surgical instruments 1A and 1B share parts and configurations other than the different portions described above.

The following is a description of the operation of the present embodiment arranged in this manner. The first and second ultrasonic surgical instruments 1A and 1B are properly used according to the applicable region and method. When the first ultrasonic surgical instrument 1A is used, the three units, the vibrator unit 2, probe unit 3, and sheath unit 4, are joined together as a proper set, as shown in FIG. 1.

Figure 3B:
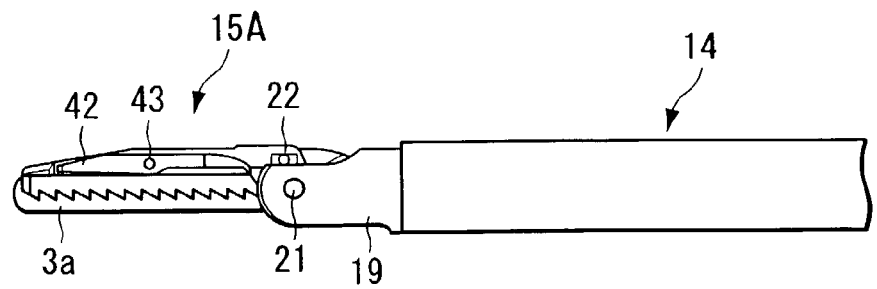
FIG. 3B is a side view of the distal operating section.

If the proper sheath 14 and the probe unit 3 are selected as the first ultrasonic surgical instrument 1A is assembled, the respective shapes of the jaw 15 and the probe tip 3a of the probe unit 3 correspond to each other. In this state, the probe unit 3 that is provided with the straight probe tip 3a shown in FIG. 5A and the sheath 14 that is provided with the substantially straight jaw 15 shown in FIGS. 3A and 3B are selected properly.

In this case, therefore, the substantially triangular engaging portion 7c of the flange portion 7 in the middle of the probe unit 3 passes on to the side of the vibrator unit 2 through the substantially triangular engaging hole portion 57c of the contact member 57 in the joint unit of the sheath 14 and the control section 16 as the proximal end portion of the probe unit 3 and the vibrator unit 2 are coupled. In this state, the proximal end portion of the probe unit 3 and the vibrator unit 2 can be coupled properly.

When the second ultrasonic surgical instrument 1B is used, moreover, the three units, the vibrator unit 2, probe unit 3, and sheath unit 4, are joined together as a proper set.

If the proper sheath 14 and the probe unit 3 are combined as the second ultrasonic surgical instrument 1B is assembled, the respective shapes of the jaw 15 and the probe tip 3a of the probe unit 3 correspond to each other. Thus, the probe unit 3 that is provided with the substantially arcuate (or curved) shaped portion 71 on its probe tip 3a, as shown in FIG. 10A, and the sheath 14 that is provided with the substantially arcuate jaw 15 corresponding to the substantially arcuate probe tip 3a of the probe unit 3, as shown in FIGS. 8A and 8B, are selected properly.

In this case, therefore, the substantially square engaging portion 7d (see FIG. 10B) of the flange portion 7 of the probe unit 3 with the same predetermined shape proper to the instrument type is combined with the substantially square engaging hole portion 57d (see FIG. 9) of the contact member 57 in the sheath 14. In this case, the substantially square engaging portion 7d of the probe unit 3 passes on to the side of the vibrator unit 2 through the substantially square engaging hole portion 57d of the contact member 57 as the proximal end portion of the probe unit 3 and the vibrator unit 2 are then coupled. In this state, the proximal end portion of the probe unit 3 and the vibrator unit 2 can be coupled properly.

The following operation is carried out if an improper combination of the sheath 14 and the probe unit 3 is selected such that the respective shapes of the jaw 15 and the probe tip 3a of the probe unit 3 fail to correspond to each other when the three units, the vibrator unit 2, probe unit 3, and sheath unit 4, are joined together.

Figure 8A:
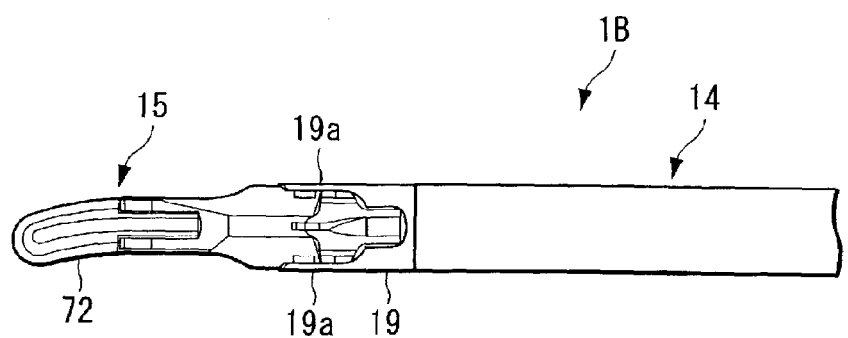
FIG. 8A is a plan view showing a distal operating section of a second ultrasonic surgical instrument of the first embodiment.
Figure 8B:
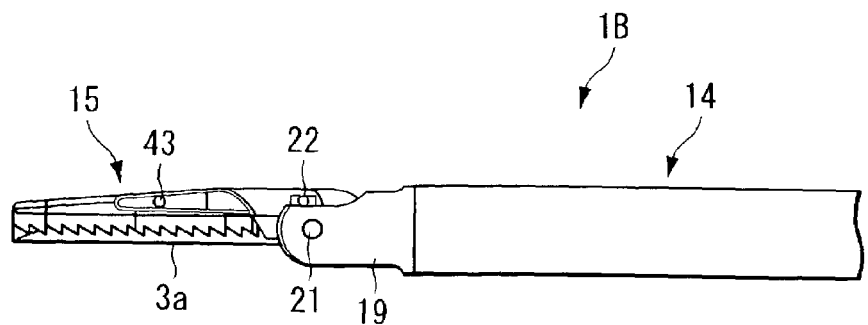
FIG. 8B is a side view of the distal operating section.
Figure 9:
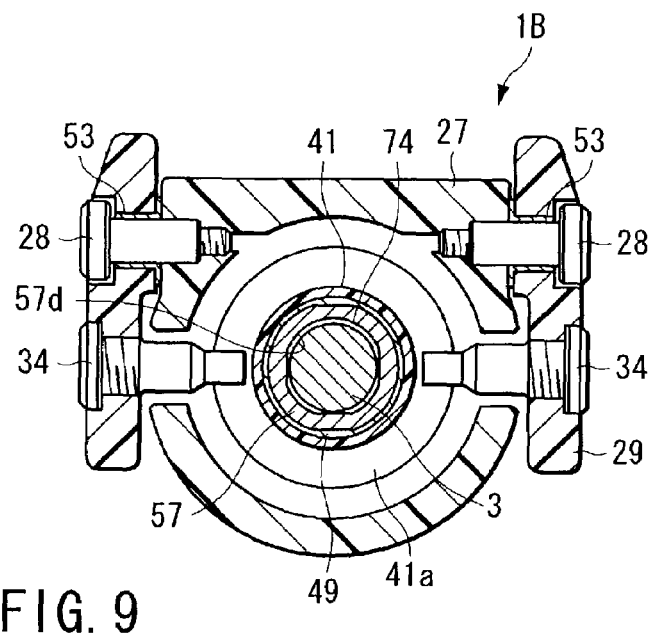
FIG. 9 is a cross-sectional view showing the way of engagement of a control section and working pins of a movable handle of the second ultrasonic surgical instrument of the first embodiment.
Figure 12A:
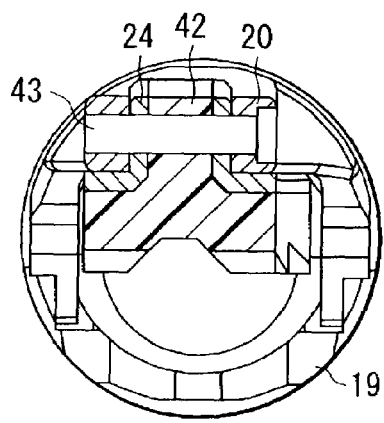
FIG. 12A is a sectional view taken along line XIIA—XIIA of FIG. 11.
Figure 12B:
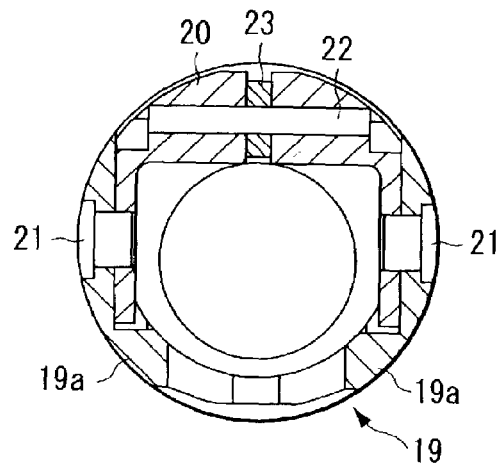
FIG. 12B is a sectional view taken along line XIIB—XIIB of FIG. 11.
Figure 13:
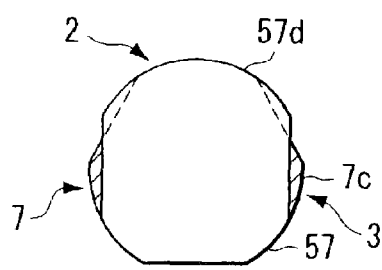
FIG. 13 is a plan view showing a flange portion of a probe of the first ultrasonic surgical instrument of the first embodiment put on that of the second ultrasonic surgical instrument.
Figure 11:
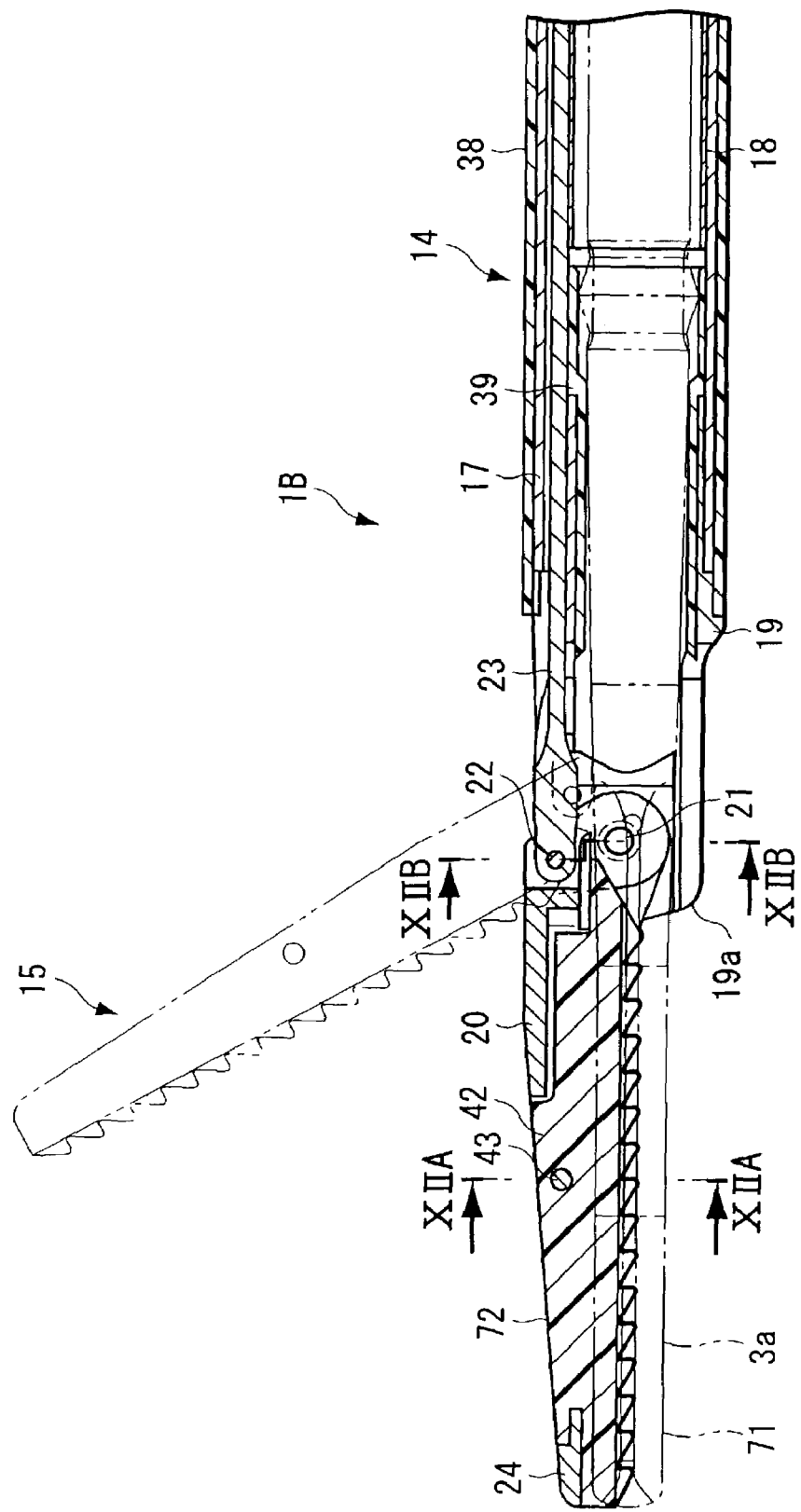
FIG. 11 is a longitudinal sectional view of the distal operating section of the second ultrasonic surgical instrument of the first embodiment.
Figure 14:
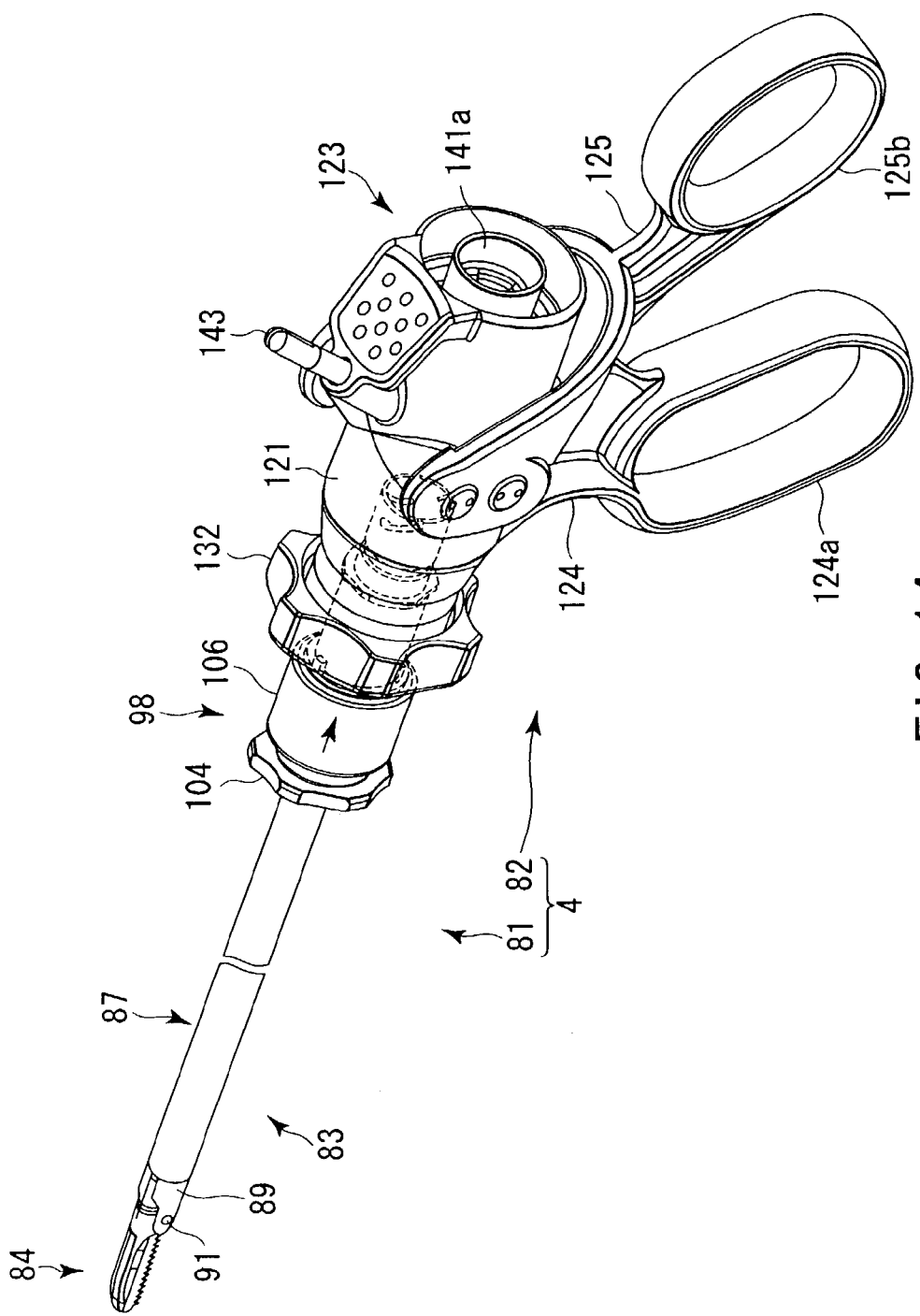
FIG. 14 is a perspective view showing the way a tip unit and a control section unit of an ultrasonic surgical instrument according to a second embodiment of the invention are joined to each other.

Let it now be supposed that the probe unit 3 that is provided with the straight probe tip 3a of the first ultrasonic surgical instrument 1A, as shown in FIG. 5, and the sheath 14 that is provided with the substantially arcuate (or curved) jaw 15 of the second ultrasonic surgical instrument 1B, as shown in FIGS. 8A and 8B, are selected individually. In this case, the substantially triangular engaging portion 7c of the flange portion 7 of the probe unit 3 proper to the instrument type is combined with the substantially square engaging hole portion 57d of the contact member 57 in the sheath 14 proper to another instrument type, as shown in FIG. 13.

In the case of this combination, the engaging portion 7c and the engaging hole portion 57d of the contact member 57 are different in shape. When the proximal end portion of the probe unit 3 and the vibrator unit 2 are then coupled to each other, therefore, an attempt must be made to join the substantially triangular engaging portion 7c of the probe unit 3 to the substantially square engaging hole portion 57d of the contact member 57. If this is done, the flange portion 7 of the probe unit 3 indicated by hatching in FIG. 13 interferes with peripheral edge portions of the substantially square engaging hole portion 57d of the contact member 57 during the joining operation, so that the former cannot pass through the latter. In this case, therefore, the proximal end portion of the probe unit 3 is prevented from passing on to the side of the vibrator unit 2.

The same interference is caused and prevents joining in the case of an inverse combination such that the probe unit 3 of the second ultrasonic surgical instrument 1B with the probe tip 3a that is formed having the substantially arcuate (or curved) shaped portion 72, as shown in FIG. 10A, and the sheath 14 of the first ultrasonic surgical instrument 1A provided with the straight jaw 15, as shown in FIGS. 3A and 3B, are selected individually.

The configuration described above produces the following effects. According to the present embodiment, the flange portion 7 of the probe unit 3 of the first ultrasonic surgical instrument 1A is provided with the engaging portion 7c having a substantially triangular cross section, and the contact member 57 of the sheath 14 into which the probe unit 3 is to be inserted is provided with the engaging hole portion 57c having a substantially triangular cross section. Further, the flange portion 7 of the probe unit 3 of the second ultrasonic surgical instrument 1B is provided with the engaging portion 7d having a substantially square cross section, and the contact member 57 of the sheath 14 into which the probe unit 3 is to be inserted is provided with the engaging hole portion 57d having a substantially square cross section.

When the proximal end portion of the probe unit 3 and the vibrator unit 2 are coupled to each other, the engaging portion 7c or 7d of the flange portion 7 at the proximal end portion of the probe unit 3 is kept so as to be able to pass through the engaging hole portion 57c or 57d of the contact member 57 on the sheath side in the case where the probe unit 3 is combined with the proper sheath 14 with the shape of the jaw 15 of the ultrasonic surgical instrument 1A or 1B corresponding to that of the probe tip 3a. In the case where the probe unit 3 is combined with the improper sheath 14 with the shape of the jaw 15 of the ultrasonic surgical instrument different from that of the probe tip 3a, the engaging portion 7c or 7d of the flange portion 7 at the proximal end portion of the probe unit 3 is not allowed to pass through the engaging hole portion 57c or 57d of the contact member 57 of the sheath side.

Thus, the probe unit 3 can be prevented from mating with the improper sheath 14 with the shape of the jaw 15 of the ultrasonic surgical instrument 1A or 1B different from that of the probe tip 3a of the probe unit 3. This enables an operator to recognize the combination to be wrong. Accordingly, the improper probe unit 3 can be prevented from being joined to the vibrator unit 2 as the three units, the vibrator unit 2, probe unit 3, and sheath unit 4, are assembled. In other words, the proper probe unit 3 can be used suitably for the region to be treated and the method of treatment.

According to the present embodiment, therefore, the vibrator unit 2, probe unit 3, and sheath unit 4 cannot be joined together unless they are compatible with one another. Thus, even in the case of an inconspicuous surgical instrument that has a thin tip operating section or insertion section for endoscopic surgical operations or delicate treatments in general surgical operations, the operator can be made aware of the wrong combination of the probe unit 3 that cannot be joined to the vibrator unit 2 at once. The operation can be started without delay by replacing the sheath unit 4 with an appropriate one.

In the case where an ultrasonic surgical instrument having a suitable tip shape for the region to be treated, method of treatment, etc., is selected for use, the vibrator unit 2, probe unit 3, and sheath unit 4 are disassembled, and the probe unit 3 and the sheath unit 4 to be used are reassembled. Even if it is hard apparently to identify a proper combination of the probe unit 3 and the sheath unit 4 from their respective tip shapes, the probe can be prevented from being joined to an incompatible handle. Thus, use of a wrong combination can be prevented. Further, a satisfactory function cannot be fulfilled if an improper combination is used. Accordingly, a troublesome operation for replacing and reassembling the probe and the handle, which is required when a wrong combination is overlooked before the start of use, can be omitted.

According to the present embodiment, moreover, the engaging portion 7c or 7d is located corresponding to a vibration node of the probe unit 3 that undergoes less vibration as the ultrasonic surgical instrument is driven. Thus, noise can be prevented from being produced at the junction between the engaging portion 7c or 7d on the outer peripheral surface of the flange portion 7 of the probe unit 3 and the engaging hole portion 57c or 57d of the contact member 57 on the sheath side.

According to the present embodiment, furthermore, metal surfaces are bonded without a gap between the engaging portion 7c or 7d on the outer peripheral surface of the flange portion 7 of the probe unit 3 and the engaging hole portion 57c or 57d of the contact member 57 on the sheath side. When the ultrasonic surgical instrument is driven, therefore, noise can be prevented from being produced at the junction between the engaging portion 7c or 7d and the engaging hole portion 57c or 57d of the contact member 57 on the sheath side.

Figure 15:
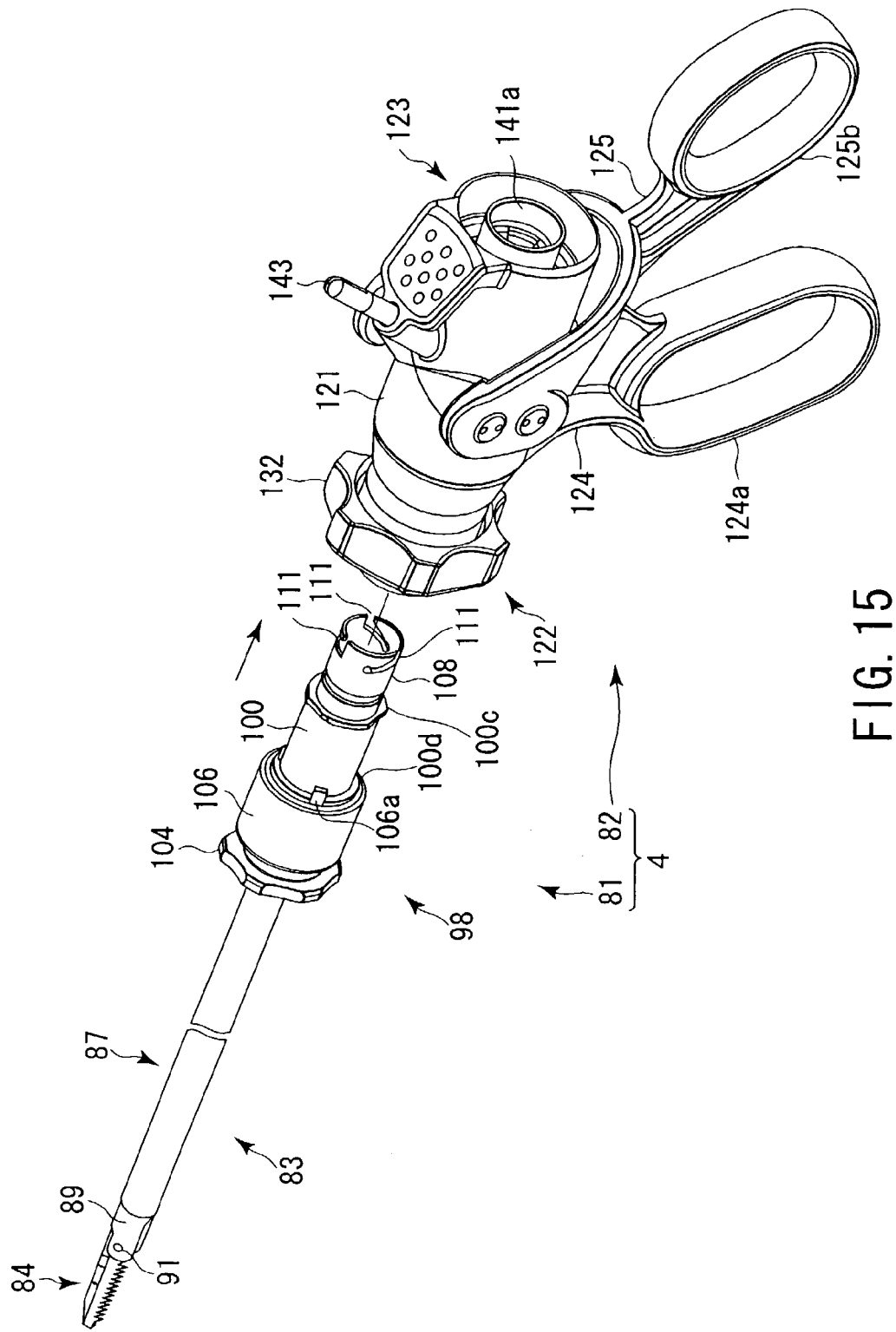
FIG. 15 is a perspective view showing a state before the tip unit and the control section unit of the ultrasonic surgical instrument of the second embodiment are joined.
Figure 16A:
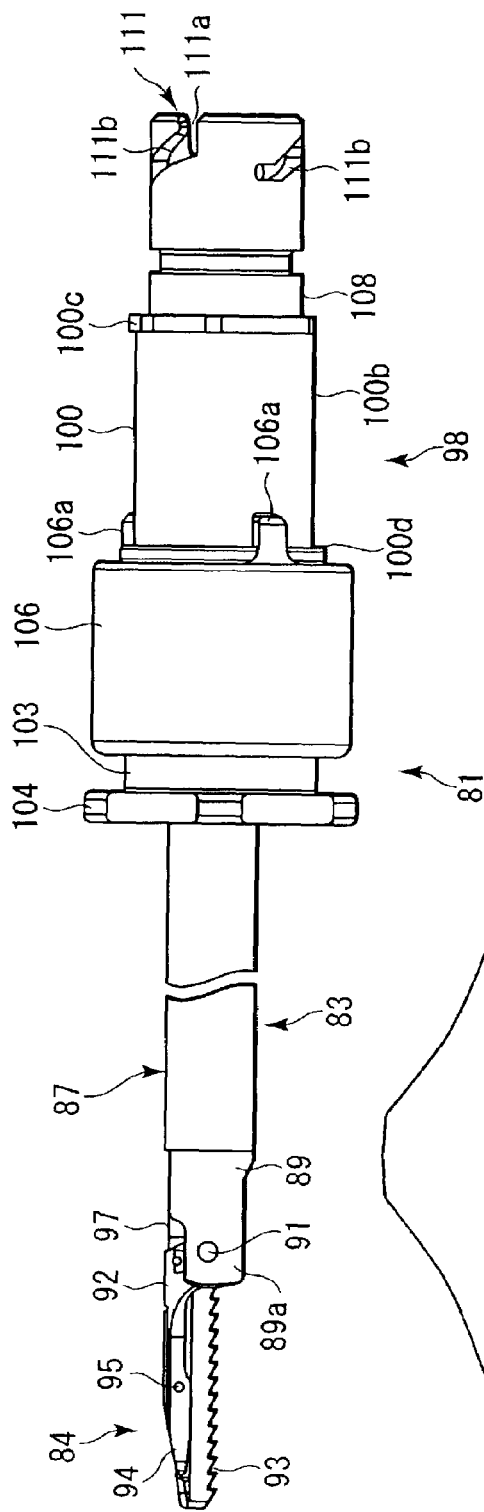
FIG. 16A is a side view showing an external appearance of the tip unit of the ultrasonic surgical instrument of the second embodiment.
Figure 16B:
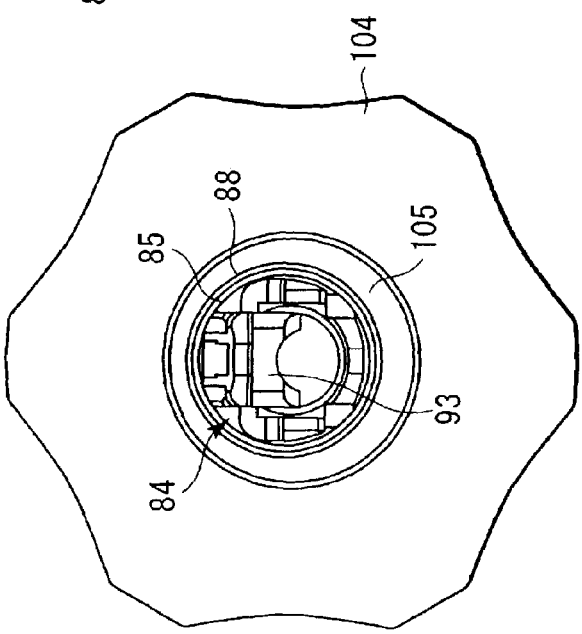
FIG. 16B is a front view of the tip unit taken from the distal end side.

FIGS. 14 to 32 show a second embodiment of the present invention. According to the second embodiment, the sheath unit 4 of the first ultrasonic surgical instrument 1A of the first embodiment (see FIGS. 1 to 13) can be further disassembled into a tip unit 81 and a control section unit 82, as shown in FIG. 15. FIGS. 16A and 16B to 22 show the tip unit 81, and FIGS. 23 to 29 show the control section unit 82.

The tip unit 81 is provided with an elongated insertion section 83 to be inserted into the body cavity in operation. A jaw 84 for use as a distal working section is provided on the distal end portion of the insertion section 83. Further, the proximal end portion of the insertion section 83 is provided with a unit coupling portion 98 (mentioned later) that is detachably coupled to the control section unit 82.

In the tip unit 81 of the second embodiment, the insertion section 83 has the same construction as the sheath unit 4 of the first embodiment. The jaw 84 of the tip unit 81 of the present embodiment is of a straight type.

Figure 19:
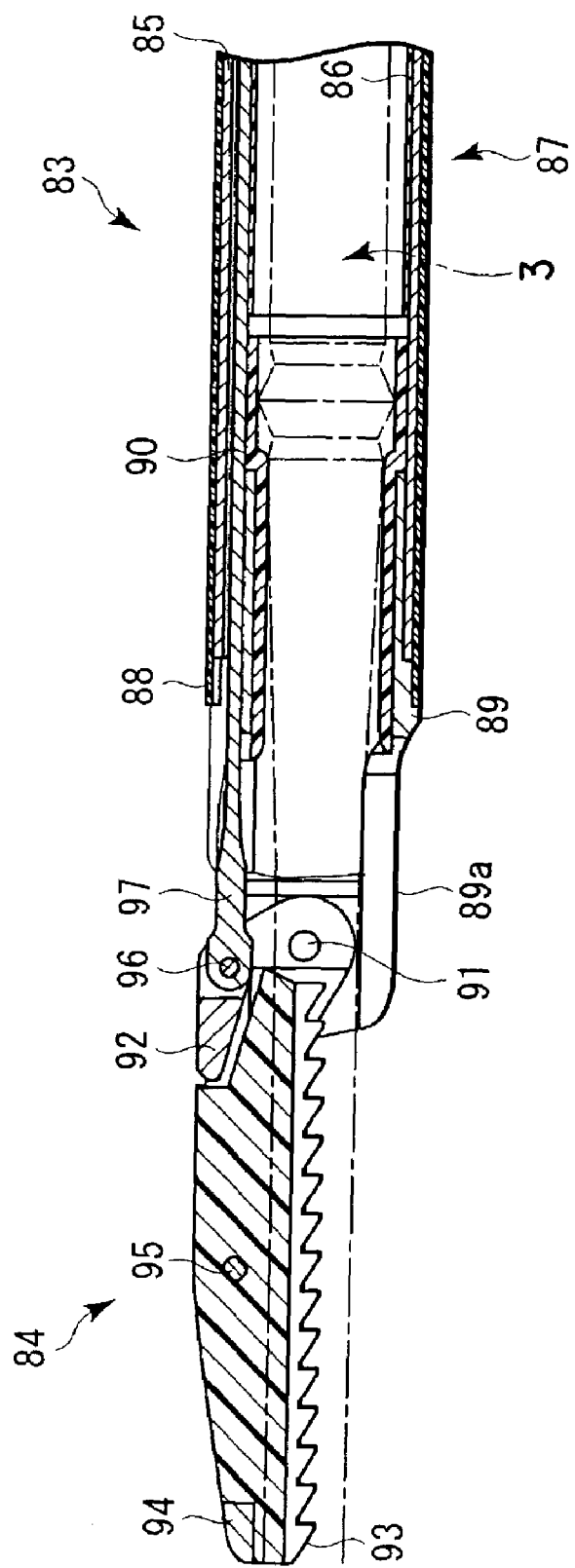
FIG. 19 is a longitudinal sectional view showing the internal construction of the distal end portion of the tip unit of the ultrasonic surgical instrument of the second embodiment.

As shown in FIG. 19, moreover, the insertion section 83 is provided with a sheath 87, which is composed of an outer pipe 85 and an inner pipe 86 with an irregular sectional shape inside the pipe 85. An insulating tube 88 covers the outside of the outer pipe 85. The tube 88 covers the pipe 85 to its proximal end portion. A channel through which the probe unit 3 is to be passed is formed inside the inner pipe 86. Further, a channel for the passage of a drive shaft 97 (mentioned later) is formed between the outer and inner pipes 85 and 86.

Figure 17:
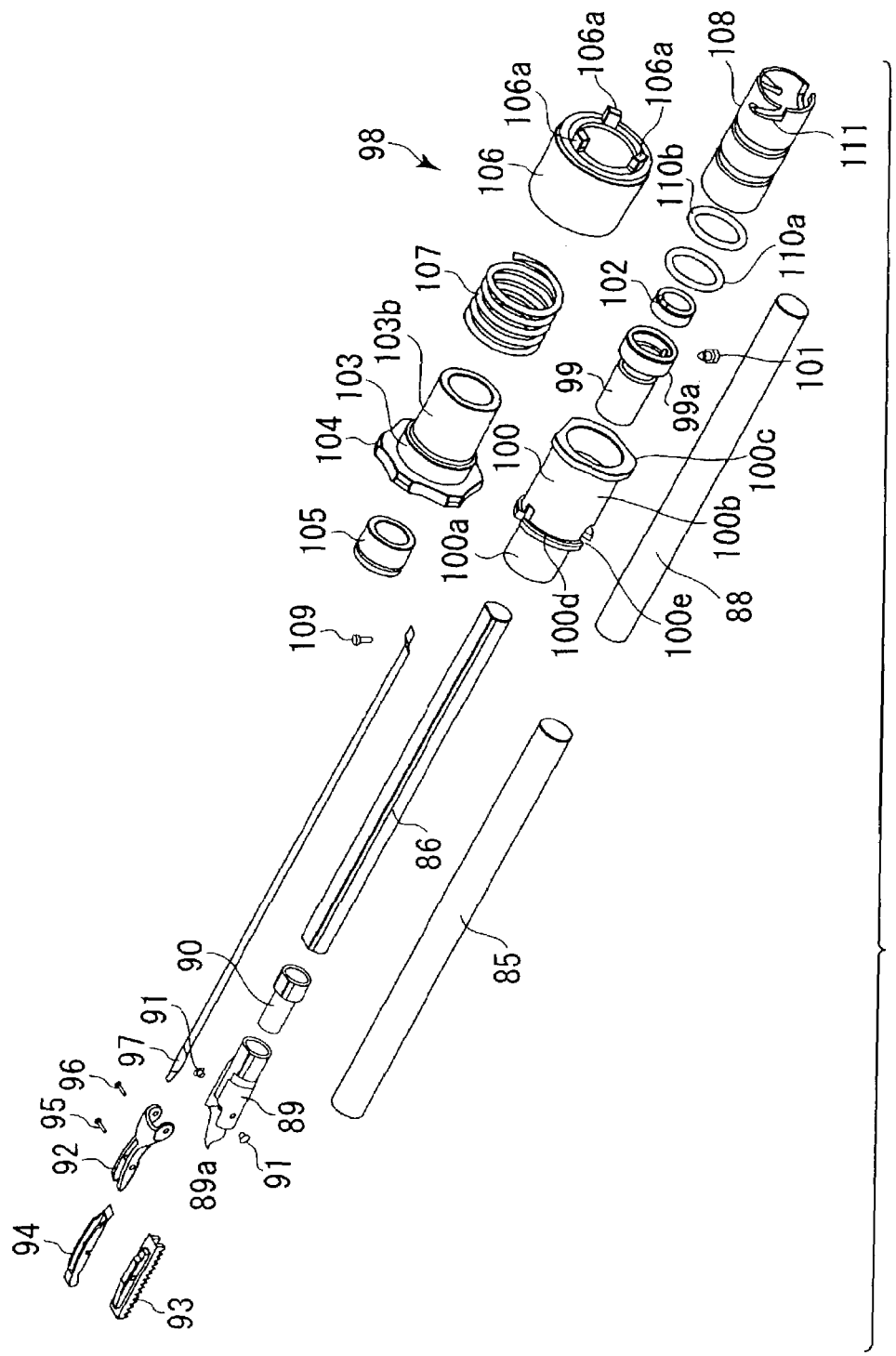
FIG. 17 is an exploded perspective view the tip unit of the ultrasonic surgical instrument of the second embodiment.

The proximal end portion of a tip cover 89 shown in FIG. 17 is fixed to the distal end side of the outer pipe 85. A pipe-shaped presser member 90 formed of a low-friction resin is attached to the inner peripheral surface side of the proximal end portion of the tip cover 89. As shown in FIG. 19, the proximal end portion of the presser member 90 extends to the outside of the tip cover 89. The presser member 90 serves to prevent the probe unit 3 indicated by the imaginary line in FIG. 19 from interfering directly with the metallic components including the tip cover 89, the outer pipe 85, drive shaft 97, etc.

Figure 18:
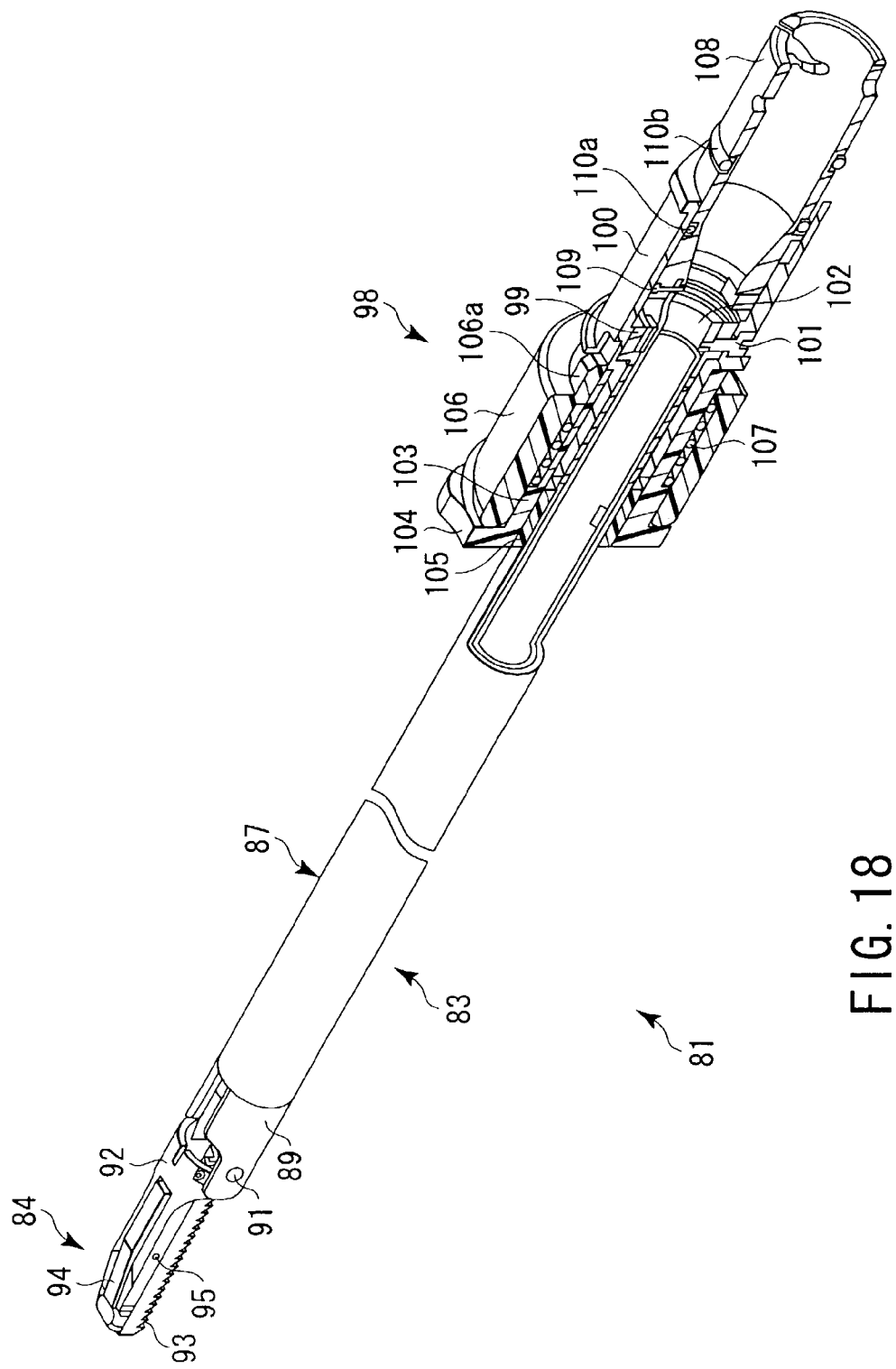
FIG. 18 is a perspective view, partially in section, showing the proximal end portion of the tip unit of the ultrasonic surgical instrument of the second embodiment.

At the distal end portion of the tip cover 89, as shown in FIG. 17, moreover, a pair of jaw supporting portions 89a, left and right, extend forward from the outer pipe 85. As shown in FIG. 18, a jaw body 92 is rockably mounted between the jaw supporting portions 89a by means of two pivot pins 91.

A holding member 93 and a holding portion mounting member 94 are mounted on the jaw body 92 by means of a pin 95 so as to be rockable through a fixed angle. As shown in FIG. 19, moreover, the distal end portion of the drive shaft 97 for transmitting driving force to open and close the jaw body 92 is coupled to the rear end of the jaw body 92 by means of a pin 96. The drive shaft 97 passes through the tip cover 89 and then between the outer and inner pipes 85 and 86 of the sheath 87, and extends to the side of the control section unit 82.

Figure 20:
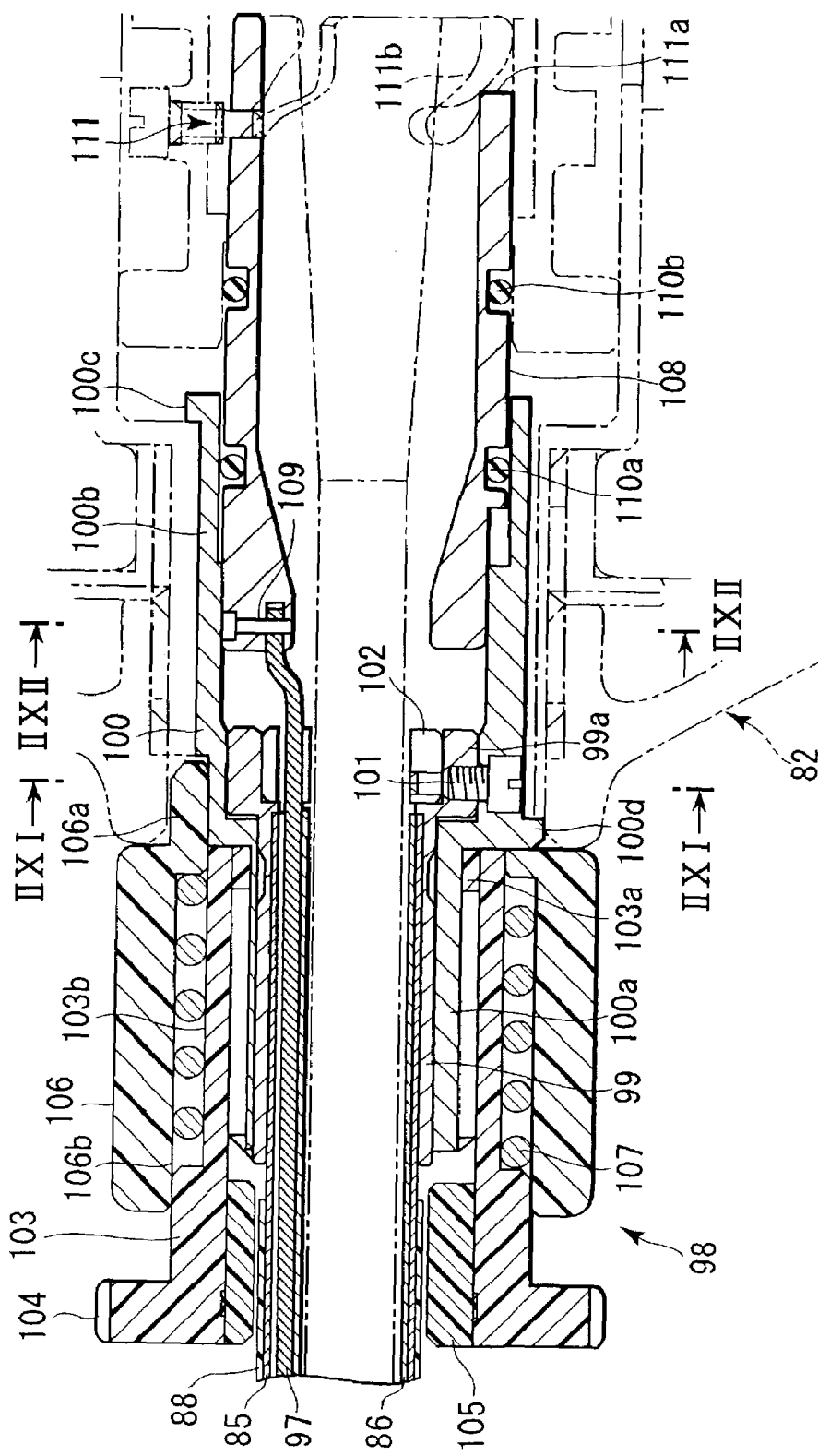
FIG. 20 is a longitudinal sectional view of a principal mechanism showing the internal construction of the proximal end portion of the tip unit of the ultrasonic surgical instrument of the second embodiment.

As shown in FIG. 20, furthermore, the unit coupling portion 98 is provided with a substantially cylindrical pipe fixing member 99 that is coupled to the proximal end portion of the outer pipe 85. The fixing member 99 is on the proximal end portion of the outer pipe 85. A large-diameter coupling ring 99a is formed on the proximal end portion of the fixing member 99.

Further, a substantially cylindrical control section connecting member 100 is located outside the pipe fixing member 99. A first coupling cylinder portion 100a that is fitted on the outer peripheral surface of the fixing member 99 is provided on the distal end side of the connecting member 100. A second coupling cylinder portion 100b that is larger in diameter than the first coupling cylinder portion 100a is located behind the cylinder portion 100a. The bore of the first cylinder portion 100a is formed of an eccentric hole. The pipe fixing member 99 is inserted into the eccentric hole of the cylinder portion 100a.

Figure 21:
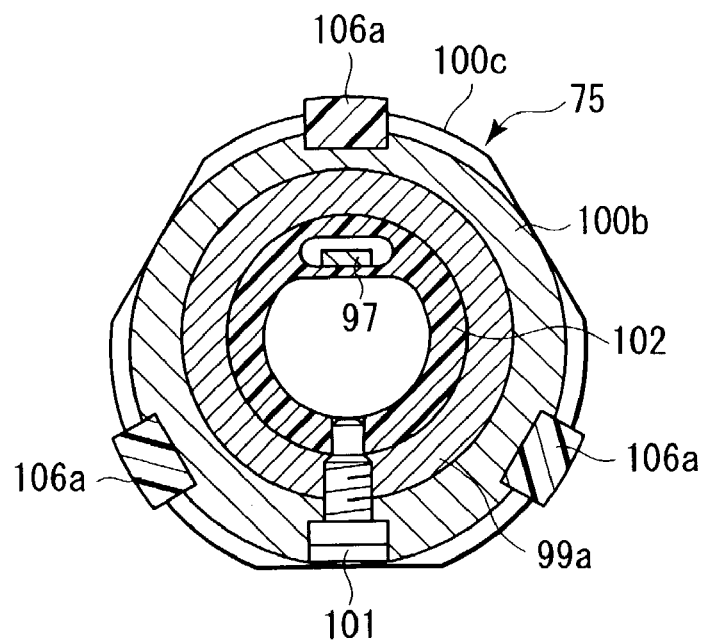
FIG. 21 is a sectional view taken along line IIXI—IIXI of FIG. 20.

As shown in FIG. 21, moreover, the inside diameter of the second coupling cylinder portion 100b is substantially equal to the outside diameter of the coupling ring 99a. The coupling ring 99a is fixed to the second coupling cylinder portion 100b of the connecting member 100 by means of a fixing screw 101. Further, a ring 102 formed of a low-friction resin is attached to the inside of the coupling ring 99a of the pipe fixing member 99 by means of the fixing screw 101. The ring 102 serves to prevent the probe unit 3 from interfering with the metallic components.

Figure 22:
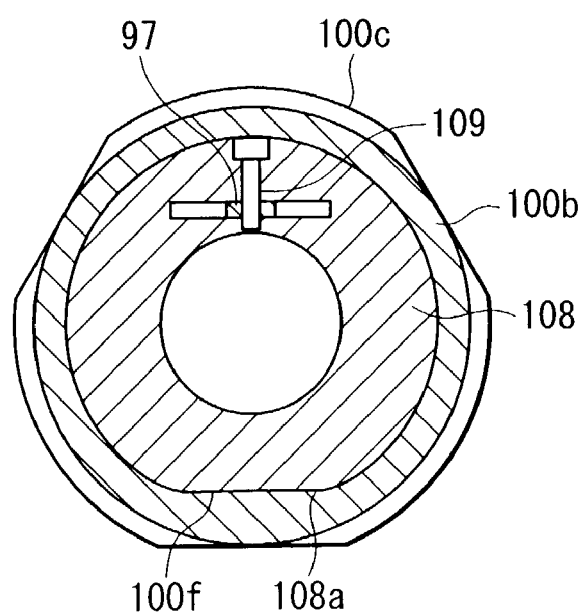
FIG. 22 is a sectional view taken along line IIXII—IIXII of FIG. 20.
Figure 23:
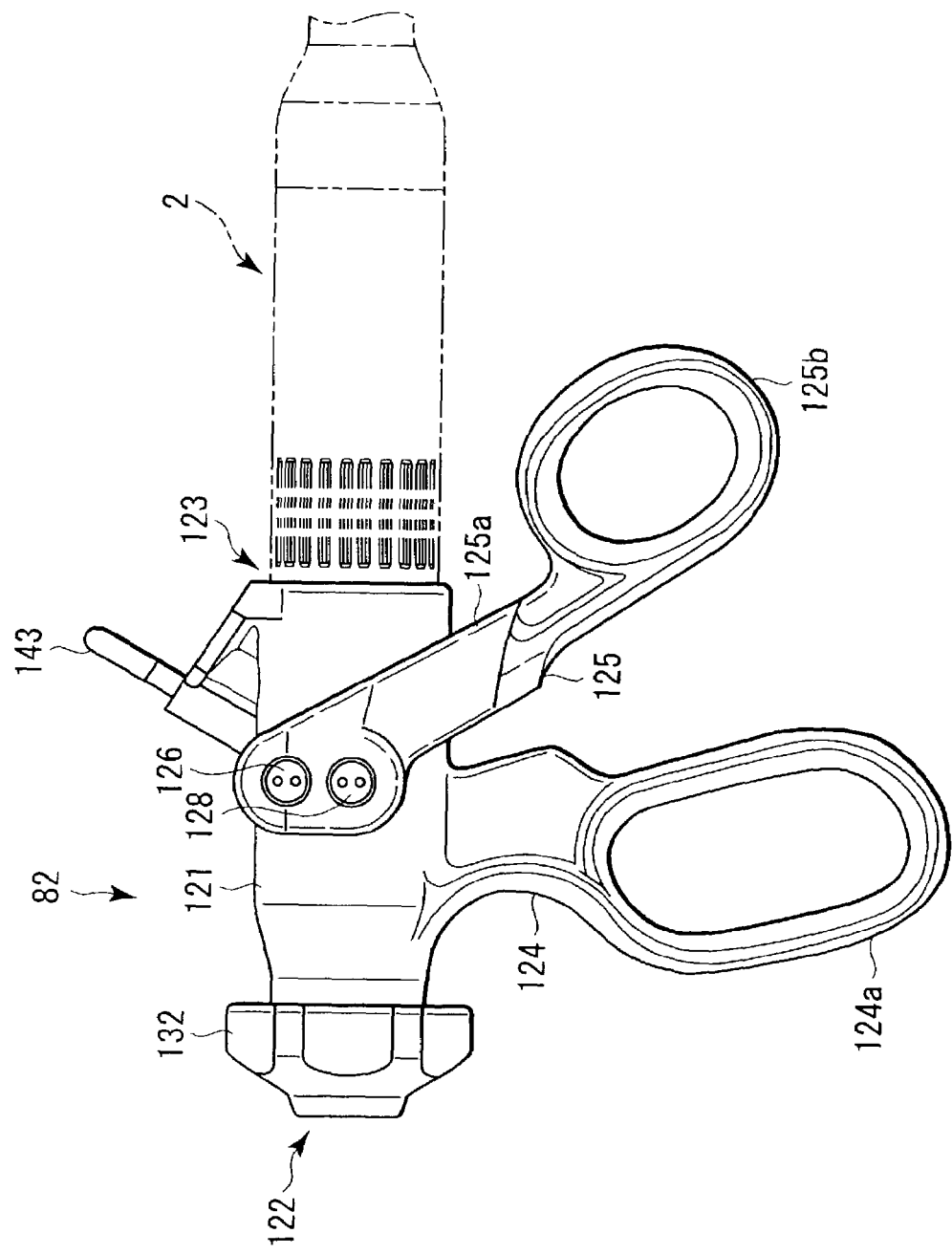
FIG. 23 is a side view showing an external appearance of the control section unit of the ultrasonic surgical instrument of the second embodiment.
Figure 24:
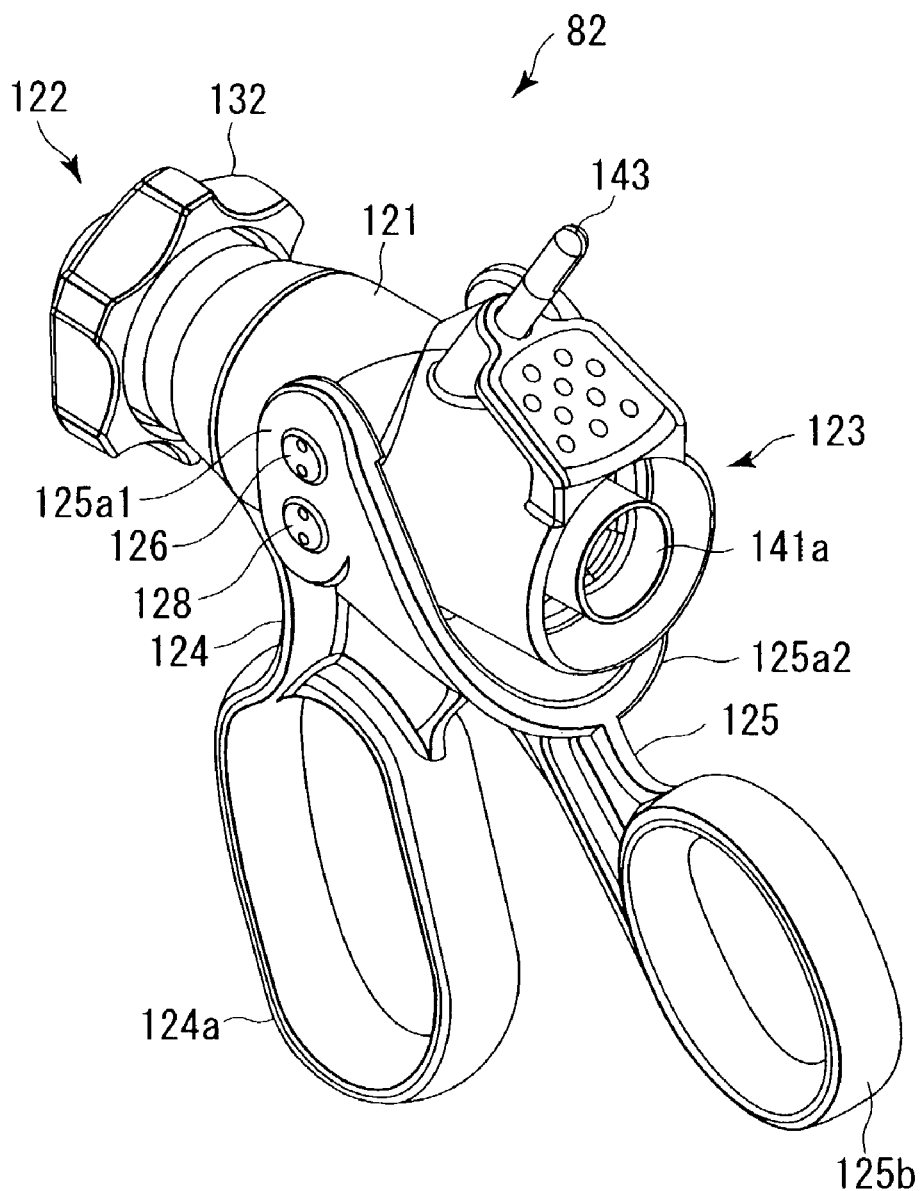
FIG. 24 is a perspective view showing an external appearance of the control section unit of the ultrasonic surgical instrument of the second embodiment.
Figure 25:
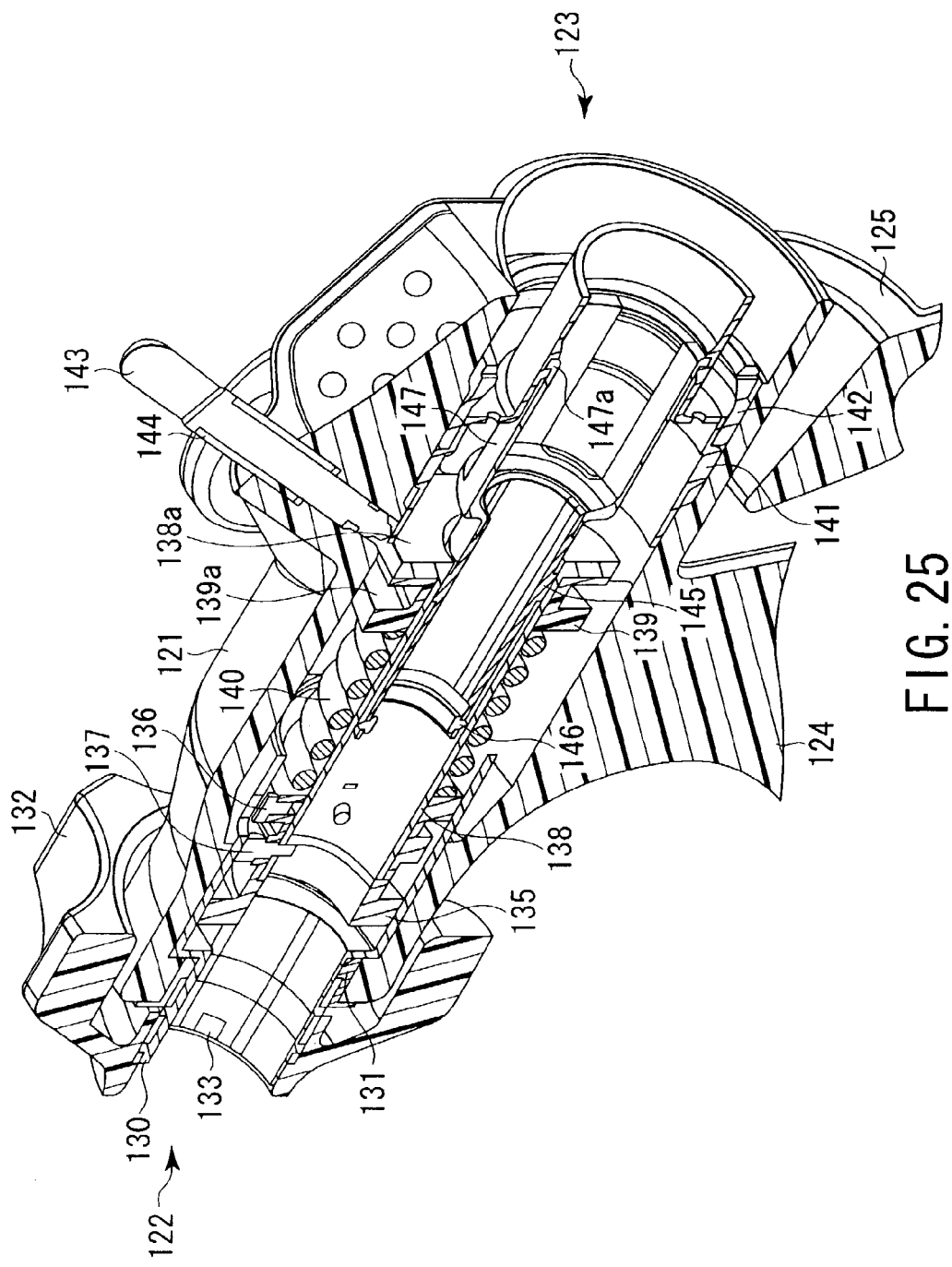
FIG. 25 is a cutaway perspective view of the control section unit of the ultrasonic surgical instrument of the second embodiment.

As shown in FIG. 22, the connecting member 100 is provided with a flange (fitting portion) 100c substantially in the shape of an equilateral triangle in the position of the rear end portion of the second coupling cylinder portion 100b. The flange 100c is designed to maintain the combination of the control section unit 82 and the handle.

On the distal end side of the connecting member 100, moreover, an intermediate flange portion 100d is provided at the junction between the first and second coupling cylinder portions 100a and 100b. The intermediate flange portion 100d has a plurality of groove portions 100e (three in number according to the second embodiment) that are arranged in the circumferential direction.

An intermediate cylinder 103 is located outside the first coupling cylinder portion 100a of the connecting member 100. A flange-shaped knob portion 104 protrudes from the distal end portion of the intermediate cylinder 103. Further, the proximal end portion of the intermediate cylinder 103 is formed having a fitting portion 103a, which is fitted on the outer peripheral surface side of the first coupling cylinder portion 100a by spline coupling, for example. A cap 105 for plugging the gap between the intermediate cylinder 103 and the insulating tube 88 is attached to the inner peripheral surface of the distal end portion of the cylinder 103.

A detent ring 106 is fitted on the intermediate cylinder 103 so as to be slidable in the axial direction of the insert section 83. A plurality of engaging claws 106a (three in number according to the present embodiment) protrude from the rear end portion of the ring 106 and are arranged in the circumferential direction. The claws 106a are located in positions corresponding individually to the groove portions 100e of the connecting member 100. The claws 106a are in engagement with their corresponding groove portions 100e.

The outer peripheral surface of the intermediate cylinder 103 is formed having a small-diameter spring mounting groove 103b that is open on the proximal end side. Further, the inner peripheral surface of the detent ring 106 is formed having a large-diameter spring mounting groove 106b that is open on the distal end side. A coil spring 107 is held between the respective spring mounting grooves 103b and 106b of the cylinder 103 and the ring 106. The detent ring 106 is mounted in a manner such that the engaging claws 106a are urged in the direction to engage the groove portions 100e of the control section connecting member 100 by means of a fixed urging force of the coil spring 107.

As the detent ring 106 is pulled in the direction opposite to the urging direction of the coil spring 107, it can slide to a position where it abuts against the knob portion 104. The detent ring 106 is sized so that the engaging claws 106a cannot be disengaged from the groove portions 100e if the ring 106 is pulled so that it runs against the knob portion 104. Thus, the detent ring 106 and the control section connecting member 100 are always kept fixed with respect to each other in the direction of rotation.

A substantially cylindrical drive shaft connecting member 108 is located in the second coupling cylinder portion 100b of the control section connecting member 100. As shown in FIG. 22, a flat notch surface 108a is formed on the outer peripheral surface of the connecting member 108. Further, an engaging hole 100f corresponding to the notch surface 108a in shape is formed in the connecting member 100. The drive shaft connecting member 108 is mounted so as to be axially slidable with respect to the connecting member 100 and fixed in the direction of rotation around the axis.

As shown in FIG. 20, the proximal end portion of the drive shaft 97 is connected to the distal end portion of the drive shaft connecting member 108. Further, two O-rings 110a and 110b are mounted on the outer peripheral surface of the connecting member 108. The one O-ring 110a is located in a position such that it can be pressed against the second coupling cylinder portion 100b of the control section connecting member 100. Further, the other O-ring 10b is located in a position such that it can be pressed against a driving force transmitting member 135 (mentioned later) when the tip unit 81 and the control section unit 82 are joined together. With the tip unit 81 joined to the control section unit 82, the O-rings 11a and 10b can prevent pneumoperitoneum gas or the like for endoscopic surgical operations from leaking out through the interior of the insert section 83.

The tip unit 81 is formed having a plurality of guide grooves 111 (three in number according to the second embodiment) on the rear end portion of the drive shaft connecting member 108. Each guide groove 111 includes a straight groove portion 111a that extends in the axial direction and a short helical groove portion 111b that winds helically. The straight groove portions 111a are arranged uniformly in the circumferential direction of the connecting member 108. Further, the proximal end portion of the helical groove portion 111b is coupled to the terminal end portion of each corresponding straight groove portion 111a.

The control section unit 82 of the second embodiment has basically the same construction as the control section 16 of the sheath unit 4 of the first embodiment. Only the construction of the mounting portion for the tip unit 81 is different from that of the first embodiment.

More specifically, the control section unit 82 of the present embodiment is provided with a substantially cylindrical control section housing 121. A tip unit coupling portion 122 and a vibrator connecting portion 123 are formed on the distal and proximal end portions, respectively, of the control section housing 121. The tip unit coupling portion 122 is detachably coupled to the tip unit 81, and the vibrator connecting portion 123 is detachably coupled to the vibrator unit 2.

Further, a stationary handle 124 is molded integrally on the outer peripheral surface of the control section housing 121. The stationary handle 124 is provided with a substantially elliptical finger loop 124a on its lower end portion.

Figure 26:
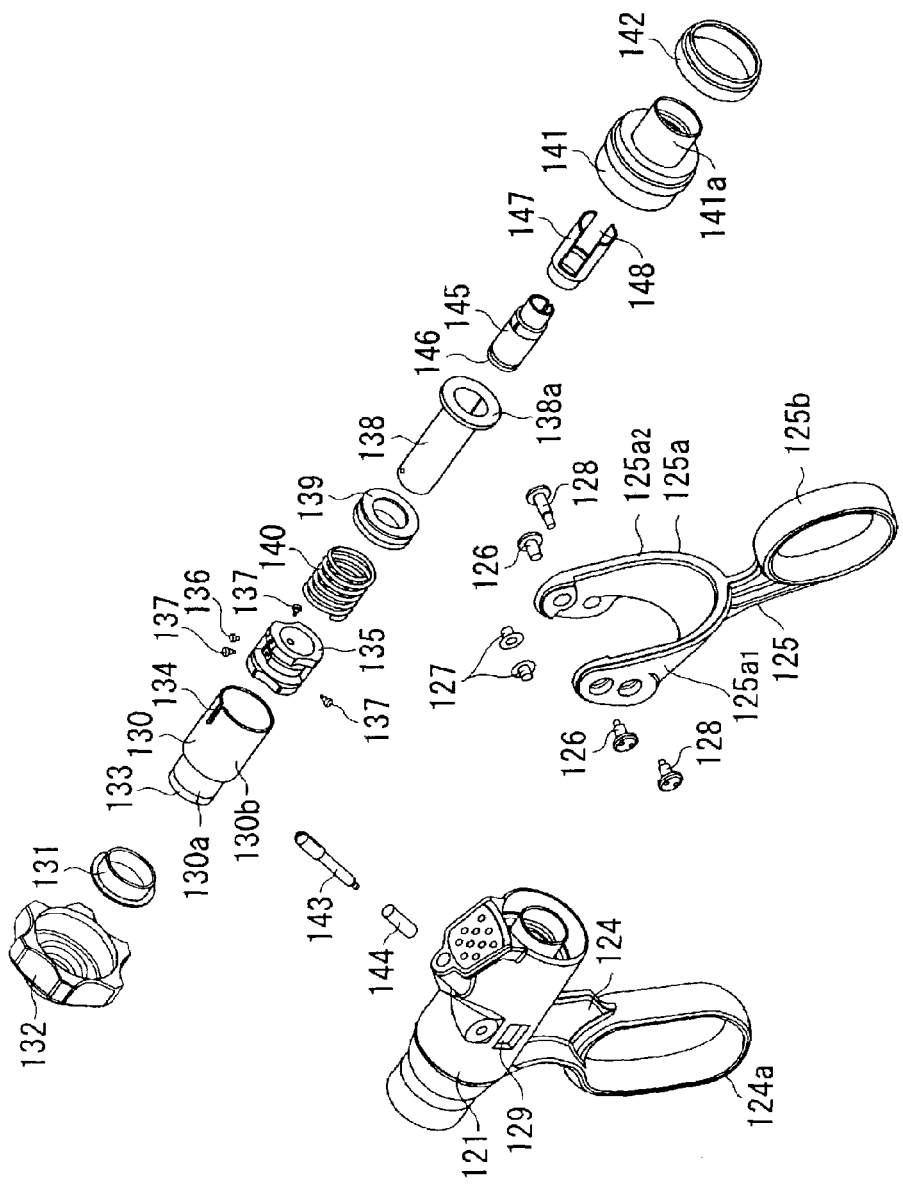
FIG. 26 is an exploded perspective view of the control section unit of the ultrasonic surgical instrument of the second embodiment.

The control section housing 121 is fitted with a movable handle 125 that can be moved toward and away from the stationary handle 124. As shown in FIG. 26, a substantially U-shaped coupling portion 125a is formed on the upper end portion of the movable handle 125. The coupling portion 125a is provided with a pair of nip portions 125a1 and 125a2 that hold the control section housing 121 from both sides.

On the opposite side faces of the control section housing 121, moreover, pivot pins 126 of the movable handle 125 are provided individually on the upper end portions of the stationary handle 124. The respective upper end portions of the nip portions 125a1 and 125a2 are rockably mounted on the upper end portion of the stationary handle 124 by means of the pivot pins 126 in a manner such that the housing 121 is held between the nip portions 125a1 and 125a2. Bushes 127 formed of low-friction PTFE or the like for better sliding performance are arranged outside the respective sliding surfaces of the pivot pins 126, individually.

Further, working pins 128 for operating force transmission protrude inward from those regions of the movable handle 125 which are situated near the pivot pins 126, individually. The windows 129 are formed of slots that extend along the respective paths of the working pins 128 that rock as the movable handle 125 rocks around the pivot pins 126. The working pins 128 of the movable handle 125 extend into the control section housing 121 through the windows 129, individually.

The movable handle 125 is provided with a substantially elliptical finger loop 125b on its lower end portion. As the handles are gripped with fingers in the loops, the movable handle 125 rocks around the pivot pins 126. Thus, the movable handle 125 can be opened and closed with respect to the stationary handle 124.

Figure 27:
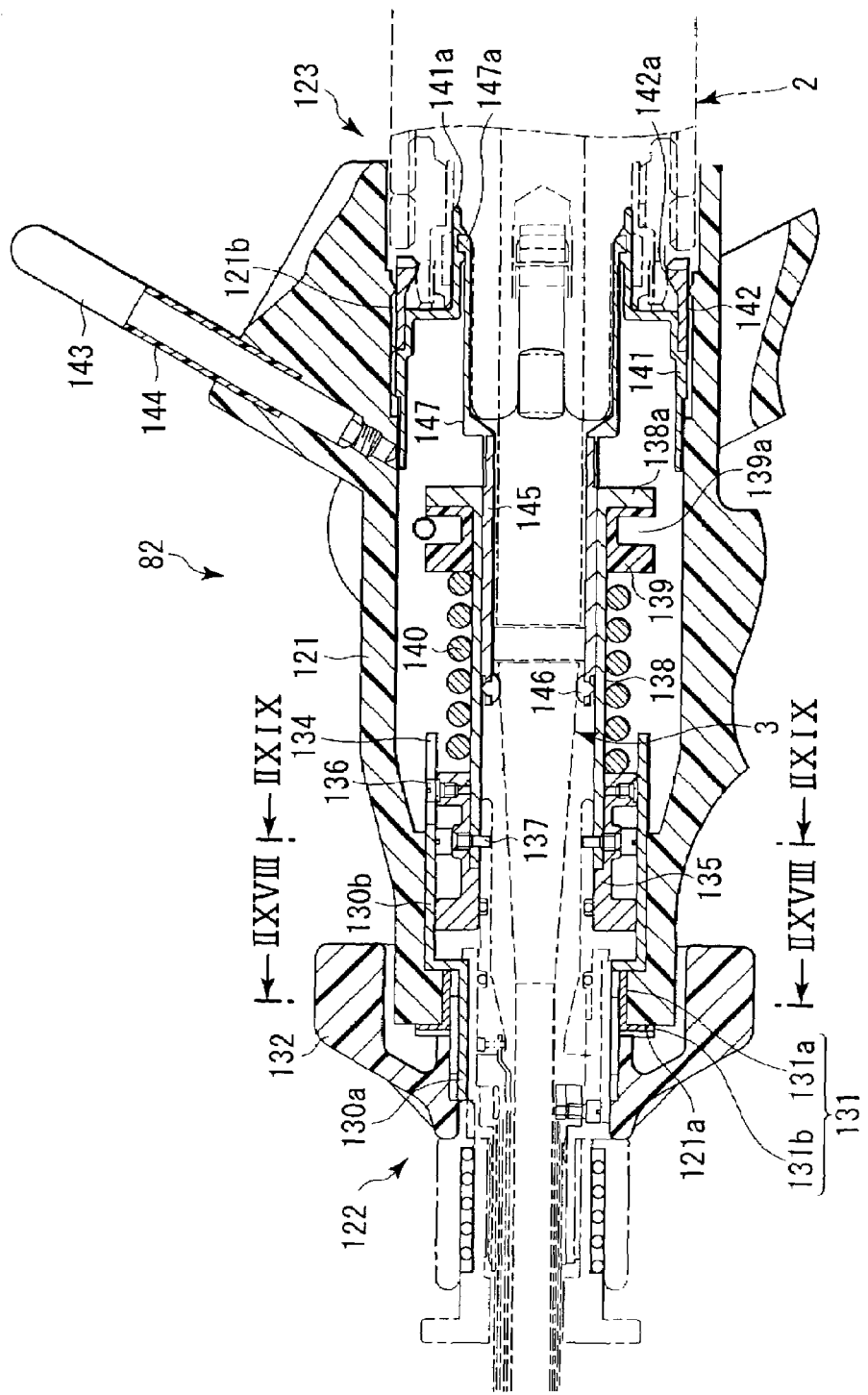
FIG. 27 is a longitudinal sectional view of a principal mechanism showing the internal construction of the control section unit of the ultrasonic surgical instrument of the second embodiment.

As shown in FIG. 27, the tip unit coupling portion 122 is provided with a substantially cylindrical tip unit connecting member 130 that is located in the control section housing 121. The connecting member 130 is formed having a small-diameter cylinder portion 130a on the distal end side and a large-diameter cylinder portion 130b behind the cylinder portion 130a.

The distal end portion of the control section housing 121 is formed having a substantially ring-shaped inside bent portion 121a that is bent inward. A step portion between the small- and large-diameter cylinder portions 130a and 130b of the tip unit connecting member 130 abuts against the inside bent portion 121a of the housing 121 from inside.

A fixing ring 131 and a rotating knob 132 are individually screwed into the small-diameter cylinder portion 130a of the tip unit connecting member 130 from the distal end side. The fixing ring 131 is formed having a bent flange portion 131b on the distal end portion of an internal threaded portion 131a that mates with the small-diameter cylinder portion 130a. The flange portion 131b of the fixing ring 131 abuts against the inside bent portion 121a of the control section housing 121 from the distal end side. The inside bent portion 121a is held between the flange portion 131b of the fixing ring 131 and the step portion between the small- and large-diameter cylinder portions 130a and 130b of the tip unit connecting member 130. The rotating knob 132 is a control member that is used to rotate the tip unit 81 around the axis when the tip unit 81 is joined to the control section unit 82.

Figure 28:
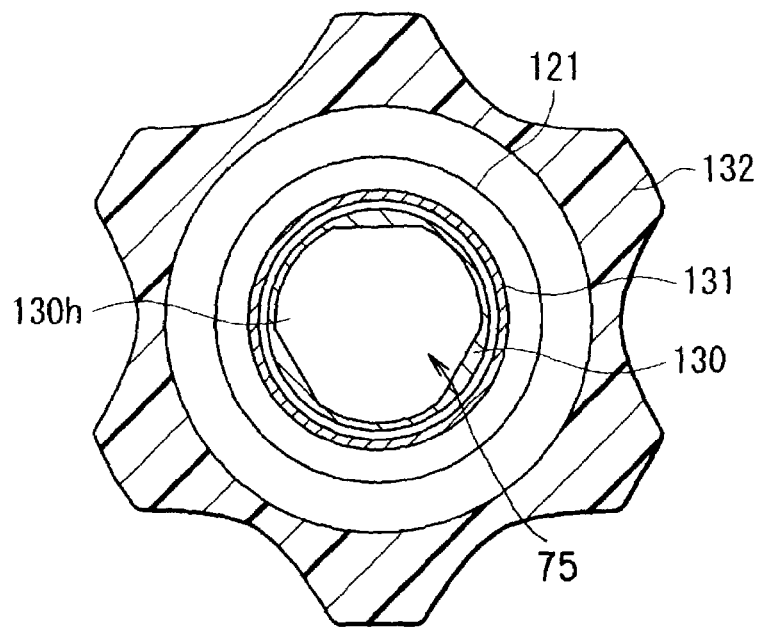
FIG. 28 is a sectional view taken along line IIXVIII—IIXVIII of FIG. 27.

As shown in FIG. 28, moreover, an engaging hole portion (fitting portion) 130h substantially in the shape of an equilateral triangle is formed on the distal end side of the tip unit connecting member 130. The hole portion 130h has the same shape as the flange 100c of the control section connecting member 100 of the tip unit 81. If the jaw 84 is has a substantially arcuate shape (curved shape), as in the case of the second ultrasonic surgical instrument 1B of the first embodiment, the flange 100c of the tip unit 81 and the engaging hole portion 130h of the control section unit 82 have substantially square sectional shapes (see FIGS. 9 and 10B), individually.

Further, the distal end portion of the tip unit connecting member 130 is formed having a plurality of engaging groove portions 133 (three in number according to the second embodiment) that are arranged in the circumferential direction. These engaging groove portions 133 are located in positions corresponding individually to the three engaging claws 106a of the detent ring 106. At the rear end portion of the connecting member 130, moreover, one engaging groove 134 extends in the axial direction of the probe unit 3.

The driving force transmitting member 135 is attached to the inside of the large-diameter cylinder portion 130b of the tip unit connecting member 130 so as to be slidable in the axial direction. A fixing pin 136 protrudes outward from the proximal end portion of the transmitting member 135. The pin 136 is fitted in the engaging groove 134 of the connecting member 130. The pin 136 serves to keep the transmitting member 135 and the connecting member 130 slidable in the axial direction and fixed in the direction of rotation around the axis.

Figure 29:
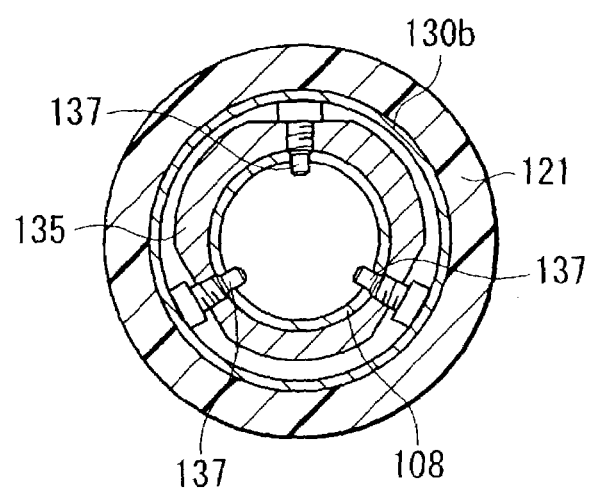
FIG. 29 is a sectional view taken along line IIXIX—IIXIX of FIG. 27.

As shown in FIG. 29, moreover, a plurality of driving force transmitting pins 137 (three in number according to the second embodiment) protrude inward from the driving force transmitting member 135. These pins 137 are arranged uniformly in the circumferential direction. Thus, the driving force transmitting pins 137 are located in positions corresponding individually to the three guide grooves 111 of the drive shaft connecting member 108 of the tip unit 81. When the tip unit 81 and the control section unit 82 are coupled to each other, the transmitting pins 137 individually engage the guide grooves 111 of the tip unit 81, and transmit driving force.

As shown in FIG. 27, furthermore, the distal end portion of a cylindrical slider receiving member 138 is attached to the rear end portion of the driving force transmitting member 135. A flange-shaped stopper portion 138a outwardly extends from the proximal end edge portion of the receiving member 138 substantially at right angles thereto.

A substantially ring-shaped slider 139 and a coil spring 140 are mounted on the outer peripheral surface of the slider receiving member 138. The slider 139 is located on the proximal end side of the receiving member 138 for axial sliding motion. Further, the coil spring 140 is set between the driving force transmitting member 135 and the slider 139 with a fixed urging force. The slider 139 is urged toward the proximal end side with a fixed force in the axial direction by means of the spring 140.

A ring-shaped engaging groove 139a is formed extending in the circumferential direction on the outer peripheral surface of the slider 139. The working pins 128 of the movable handle 125 are fitted in the engaging groove 139a. Thus, the slider 139 is caused to engage the handle 125 by means of the pins 128. Operating force for opening and closing the movable handle 125 is converted into axial movement of the slider 139 by means of the working pins 128.

As shown in FIG. 27, a tapped hole 121b is formed in the rear end portion of the control section housing 121. A substantially cylindrical guide member 141 and a ring receiving member 142, which constitute the vibrator connecting portion 123, are individually screwed into the tapped hole 121b.

Further, the rear end portion of the guide member 141 is formed having a small-diameter connecting cylinder portion 141a that can be inserted into the attachment 10 of the vibrator unit 2. A vibrator unit engaging groove is formed between the cylinder portion 141a of the guide member 141 and the ring receiving member 142. An engaging protuberance 142a protrudes inward from the inner peripheral surface of the rear end portion of the receiving member 142. The protuberance 142a is smaller in diameter than the C-ring 11 of the attachment 10 of the vibrator unit 2.

When the sheath unit 4 and the vibrator unit 2 are coupled to each other, the attachment 10 of the vibrator unit 2 can be removably inserted into the vibrator unit engaging groove between the connecting cylinder portion 141a of the guide member 141 and the ring receiving member 142. As the C-ring 11 is elastically deformed to get over the engaging protuberance 142a of the receiving member 142, in this state, the sheath unit 4 and the vibrator unit 2 are caused to detachably engage each other.

Further, a backwardly leaning electric cord connecting pin 143 is attached to the outer peripheral surface of the rear end portion of the control section housing 121. The active cord (not shown) for supplying high-frequency current from the high-frequency cautery power source unit (not shown) is connected to the connecting pin 143.

Furthermore, an insulating pin cover 144 for securing electrical insulation with the active cord on the electrical cord connecting pin 143 is attached to the proximal end portion of the pin 143. The proximal end portion of the pin 143 is in contact with and connected electrically to the guide member 141.

A substantially cylindrical first contact member 145 for electrical conduction to the probe unit 3 is inserted into the cylinder of the slider receiving member 138 through its rear end portion. A conductive rubber ring member 146 is formed on the distal end portion of the first contact member 145 by insert molding or the like. The inner peripheral surface side of the ring member 146 forms a part that touches the probe unit 3. Further, the outer peripheral surface of the ring member 146 has the form of packing that is pressed against the inner peripheral surface of the receiving member 138 to prevent leakage of pneumoperitoneum gas or the like. The first contact member 145 and the receiving member 138 are kept fixed or nonrotatable around the axis with respect to each other, as in the case of the first embodiment.

Further, the distal end portion of a second contact member 147 is fixed to the rear end of the first contact member 145. The proximal end portion of the second contact member 147 is formed having slit portions 148 that extend in the axial direction. At the proximal end portion of the second contact member 147, a projection 147a protrudes outward from the tube wall portions between the slit portions 148. As shown in FIG. 27, the projection 147a engages a groove portion on the inside of the guide member 141 and is immovable in the axial direction.

The outside diameter of the tube wall portions between the slit portions 148 of the proximal end portion of the second contact member 147 is a little larger than the inside diameter of the guide member 141. When the second contact member 147 and the guide member 141 are joined together, they are fixed and connected electrically to each other as the tube wall portions between the slit portions 148 are elastically deformed.

The following is a description of the operation of the second embodiment arranged in this manner. The sheath unit 4 is assembled at the start of use of the ultrasonic surgical instrument 1A of the present embodiment. In assembling the sheath unit 4, the tip unit 81 is joined to the control section unit 82.

In joining the tip unit 81 to the control section unit 82, the flange 100c of the control section connecting member 100 of the tip unit 81 is first oriented to get it into the engaging hole portion 130h of the tip unit connecting member 130. In the second embodiment, the engaging hole portion 130h and the flange 100c of the connecting member 100 of the tip unit 81 are both substantially in the shape of an equilateral triangle, so that the tip unit 81 and the control section unit 82 can be joined in three rotational positions at circumferential offsets of 120°.

The unit coupling portion 98 of the tip unit 81 is axially inserted straight into a distal opening portion of the tip unit coupling portion 122 of the control section unit 82, as shown in FIG. 15, with the engaging hole portion 130h aligned with the flange 100c of the control section connecting member 100 of the tip unit 81. As this is done, the tip unit 81 is inserted into the engaging hole portion 130h of the control section unit 82 through the drive shaft connecting member 108.

As the tip unit 81 is further inserted in this state, the flange 100c of the control section connecting member 100 is inserted into the substantially triangular engaging hole portion 130h of the inside the tip unit connecting member 130 if the combination of the tip unit 81 and the control section unit 82 is proper. As the tip unit 81 then continues to be inserted, the engaging claws 106a of the detent ring 106 engage and abut against the end portion of the tip unit connecting member 130 in the rotating knob 132 of the control section unit 82 and are pushed toward the distal end side. As this is done, the detent ring 106 is pushed out to the distal end portion side, resisting the urging force of the coil spring 107. If the engaging hole portion 130h and the flange 100c have different shapes, the flange 100c runs against the peripheral edge region of the engaging hole portion 130h, whereupon the insertion of the tip unit 81 is prevented thereafter. Accordingly, the tip unit 81 and the control section unit 82 can be prevented from being joined in a wrong combination. When the tip unit 81 and the control section unit 82 are joined together, therefore, the fitting portion between the engaging hole portion 130h of the tip unit connecting member 130 and the flange 100c of the connecting member 100 forms an incompatible joining preventing portion 75. The preventing portion 75 allows the units 81 and 82 for the same instrument type to be joined together and prevents the probe unit 3 for a different instrument type from being joined.

If the tip unit 81 is further inserted straight in the axial direction with the flange 100c of the control section connecting member 100 in the engaging hole portion 130h of the tip unit connecting member 130, moreover, the flange 100c passes through the hole portion 130h to the proximal end portion side. Thereupon, the tip unit 81 is allowed to rotate around the axis.

If the entire tip unit 81 is rotated around the axis in this state, the engaging claws 106a reach positions corresponding individually to the engaging groove portions 133 of the tip unit connecting member 130. Since the detent ring 106 is urged toward the proximal end portion by means of the urging force of the coil spring 107 in this state, the claws 106a are caused to engage with the engaging groove portions 133, individually, as shown in FIG. 31. In FIG. 31, two-dot chain lines indicate the state of the engaging claws 106a before the entire tip unit 81 is rotated bout the axis.

Thus, in disassembling the tip unit 81 and the control section unit 82, the tip unit connecting member 130 in the control section unit 82 and the control section connecting member 100 of the tip unit 81 cannot rotate with respect to each other unless the detent ring 106 is axially pulled to the distal end.

When the engaging claws 106a are in engagement with the engaging groove portions 133, as shown in FIG. 31, moreover, the rotated flange 100c of the control section connecting member 100 is in the position indicated by the two-dot chain line in FIG. 32. Thus, the flange 100c forms three catch portions between itself and the peripheral edge region of the engaging hole portion 130h. These three catch portions serve to prevent the tip unit 81 from axially slipping out toward the distal end.

If the rotating knob 132 is rotated, therefore, the tip unit 81 is also rotated as a follower by means of the tip unit connecting member 130, detent ring 106, and control section connecting member 100 in succession.

If the tip unit 81 is inserted further, the three driving force transmitting pins 137 of the control section unit 82 get individually into the straight groove portions 111a of the guide grooves 111 of the drive shaft connecting member 108. In this state, the tip unit 81 is inserted straight into the position where the pins 137 abut individually against the respective terminal end portions of the groove portions 111a.

Figure 30:
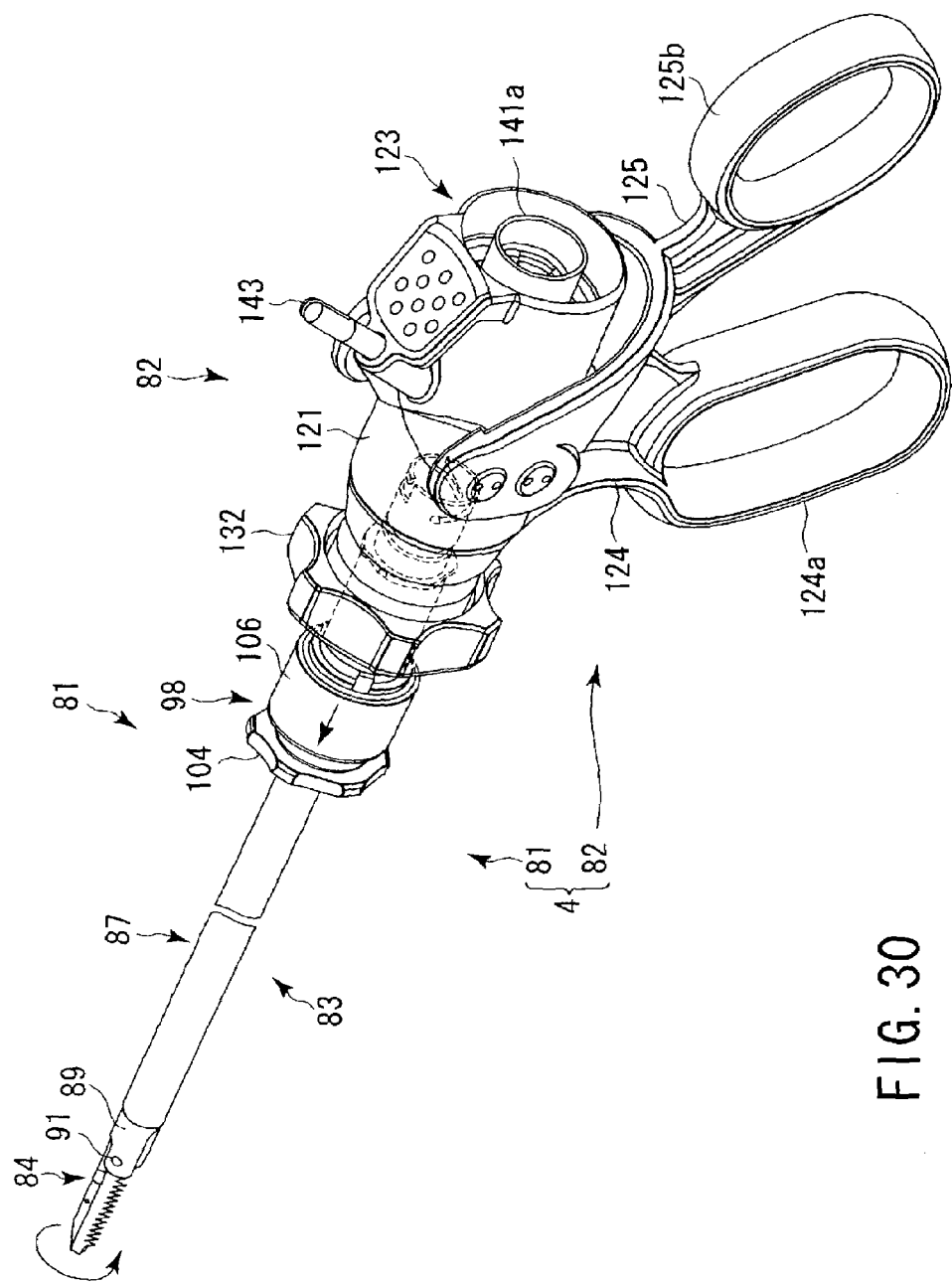
FIG. 30 is a perspective view showing the way the tip unit and the control section unit of the ultrasonic surgical instrument of the second embodiment are joined to each other.

When the driving force transmitting pins 137 run against the respective terminal end portions of the straight groove portions 111a, moreover, the entire tip unit 81 is rotated about the axis, as indicated by arrow in FIG. 30. When this is done, the pins 137 are guided by the respective helical groove portions 111b of the guide grooves 111 as they move. Accordingly, the tip unit 81 rotates about the axis and along the helical groove portions 111b as they are inserted in the axial direction. When the driving force transmitting pins 137 are then pulled in and moved to the terminal end position of the helical groove portions 111b of the guide grooves 111 by the cam-groove system, they are caused to engage fixedly in the axial direction. Thus, joining the tip unit 81 and the control section unit 82 is completed.

If the movable handle 125 of the control section unit 82 is operated in this state, driving force is transmitted to the drive shaft connecting member 108 via the slider 139, slider receiving member 138, driving force transmitting member 135, and driving force transmitting pins 137 in the order named. Thereupon, the jaw 84 at the distal end portion is opened or closed.

In joining the tip unit 81 and the control section unit 82 together, moreover, the one O-ring 110a that is mounted on the drive shaft connecting member 108 of the tip unit 81 indicated by the two-dot chain line in FIG. 27 is kept pressed against the second coupling cylinder portion 100b of the control section connecting member 100. On the other hand, the other O-ring 110b is kept pressed against the driving force transmitting member 135 of the control section unit 82. Thus, the O-rings 110a and 110b can prevent pneumoperitoneum gas from leaking out through the gap between the connecting member 108 and the second coupling cylinder portion 100b of the connecting member 100 or between the connecting member 108 and the driving force transmitting member 135 of the control section unit 82.

In the case where the jaw 84 of the tip unit 81, like that of the second ultrasonic surgical instrument 1B of the first embodiment, is curved (see FIG. 8A), the respective hole shapes of the flange 100c of the control section connecting member 100 and the tip unit connecting member 130 of the second embodiment are set in the same manner as the flange shape of the second ultrasonic surgical instrument 1B of the first embodiment. Thus, the tip unit 81 and the control section unit 82 of the first ultrasonic surgical instrument 1A having the straight jaw 84 can be prevented from being wrongly combined with those of the second ultrasonic surgical instrument 1B having the curved jaw 84.

The configuration described above produces the following effects. According to the second embodiment, the sheath unit 4 of the first ultrasonic surgical instrument 1A of the first embodiment can be further disassembled into the tip unit 81 and the control section unit 82, as shown in FIG. 15. FIGS. 16A and 16B to 22 show the tip unit 81, and FIGS. 23 to 29 show the control section unit 82. In the first ultrasonic surgical instrument 1A of the second embodiment, the holding member 93 of the tip unit 81 is wears most easily, in general. Parts other than the tip unit 81 have higher durability. Accordingly, the high-durability parts other than the tip unit 81 can continue to be used without being replaced with new ones if only the tip unit 81 is replaced. Thus, the cost of surgical operations can be made lower than in the case where the ultrasonic surgical instrument is replaced entirely.

In the first ultrasonic surgical instrument 1A of the second embodiment, moreover, the flange 100c of the tip unit 81 and the engaging hole portion 130h of the control section unit 82 have a cross section substantially in the shape of an equilateral triangle. In the case of the second ultrasonic surgical instrument 1B, the flange 100c and the engaging hole portion 130h have a substantially square cross section.

Thus, also in the second embodiment, the tip unit 81 and the control section unit 82 can be prevented from being joined in a wrong combination as they are assembled. Consequently, the tip unit 81 and the control section unit 82 can maintain a proper combination, and the ultrasonic surgical instruments can be properly used according to the region to be treated and the method of treatment.

The present invention is not limited to the embodiments described above. The invention is also applicable to an ultrasonic surgical instrument without any distal working section, such as the ones attached to the ultrasonic surgical instruments of the foregoing embodiments. In this case, the instrument can be held like a pen as it is operated. It is to be understood, moreover, that various changes and modifications may be effected in the invention without departing from the scope or spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic surgical instrument comprising:
    a common unit formed to be usable in common with a plurality of types of instruments;
    a first individual unit couplable to the common unit and used for a first treatment, the first individual unit including a first functional portion having a function to perform the first treatment, and a first engagement portion engageable with the first functional portion of the first individual unit;
    a second individual unit couplable to the common unit and used for a second treatment, the second individual unit including a first functional portion having a function to perform the second treatment, and a second engagement portion engageable with the first functional portion of the second individual unit; and
    an incompatible joining preventing portion provided in the first individual unit and capable of preventing the second engagement portion from being engaged with the first functional portion of the first individual unit.

2. An ultrasonic surgical instrument according to claim 1, wherein
    the first functional portion of the first individual unit is formed of a probe unit having a probe tip capable of transmitting ultrasonic vibration,
    the first engagement portion is formed of a sheath unit including a sheath having a passage through which the probe unit can pass, and
    the incompatible joining preventing portion is provided in a connection part between the probe unit and the sheath unit and is a probe insertion preventing unit adapted to allow the insertion of only the probe unit of the same instrument type and prevent the insertion of a probe unit of a different type when the probe unit passes through the passage of the sheath unit.

3. An ultrasonic surgical instrument according to claim 2, wherein the probe insertion preventing unit has fitting portions in a part of the passage of the sheath unit, the respective sectional shapes of the fitting portions are exclusive depending on the instrument type.

4. An ultrasonic surgical instrument according to claim 3, wherein the fitting portions are located corresponding to vibration nodes of the probe unit.

5. The ultrasonic surgical instrument of claim 1 wherein:
the first engagement portion is a first sheath unit, the first sheath unit including a first sheath and a first operating unit functional portion detachably mounted to the first sheath;
the second engagement portion is a second sheath unit, the second sheath unit including a second sheath and a second operating unit functional portion detachably mounted to the second sheath; and a second incompatible joining preventing portion is provided in the first sheath unit and is capable of preventing the second operating unit portion from being mounted to the first sheath unit.

* * * * *